(12) United States Patent
Hunt et al.

(10) Patent No.: US 8,293,721 B2
(45) Date of Patent: Oct. 23, 2012

(54) CETP INHIBITORS DERIVED FROM BENZOXAZOLE ARYLAMIDES

(75) Inventors: Julianne A. Hunt, Montclair, NJ (US); Ramzi F. Sweis, Franklin Park, NJ (US); Peter J. Sinclair, Scotch Plains, NJ (US)

(73) Assignee: Merck Sharpe & Dohme Corp., Rahway, NJ (US)

( * ) Notice: Subject to any disclaimer, the term of this patent is extended or adjusted under 35 U.S.C. 154(b) by 151 days.

(21) Appl. No.: 12/664,815

(22) PCT Filed: Jun. 16, 2008

(86) PCT No.: PCT/US2008/007471
§ 371 (c)(1),
(2), (4) Date: Dec. 15, 2009

(87) PCT Pub. No.: WO2008/156718
PCT Pub. Date: Dec. 24, 2008

(65) Prior Publication Data
US 2010/0184719 A1 Jul. 22, 2010

Related U.S. Application Data

(60) Provisional application No. 60/936,534, filed on Jun. 20, 2007.

(51) Int. Cl.
*A61K 31/714* (2006.01)
*A61K 31/4439* (2006.01)
*A61K 31/444* (2006.01)
*A61K 31/506* (2006.01)
*C07D 413/14* (2006.01)
*C07D 413/12* (2006.01)

(52) U.S. Cl. .......... 514/52; 514/529; 514/275; 514/333; 514/338; 514/356; 546/271.7; 546/256; 548/224

(58) Field of Classification Search .................. None
See application file for complete search history.

(56) References Cited

U.S. PATENT DOCUMENTS

| 4,831,152 A | 5/1989 | Itoh et al. |
| 6,355,441 B1 | 3/2002 | Edwards et al. |
| 2006/0040999 A1 | 2/2006 | Ali et al. |

FOREIGN PATENT DOCUMENTS

| WO | WO 96/11917 | 4/1996 |
| WO | WO 00/45819 | 8/2000 |
| WO | WO01/00587 | 1/2001 |
| WO | WO 01/14354 A1 | 3/2001 |
| WO | WO 2007/070173 A2 | 6/2007 |
| WO | WO 2008/156715 A1 | 12/2008 |
| WO | WO 2008/156717 A1 | 12/2008 |

OTHER PUBLICATIONS

Supplemental European Search Report (Munich); Performed—Jun. 22, 2011.

*Primary Examiner* — Kamal Saeed
(74) *Attorney, Agent, or Firm* — James L. McGinnis; Catherine D. Fitch

(57) ABSTRACT

Compounds having the structure of Formula I, including pharmaceutically acceptable salts of the compounds, are potent CETP inhibitors, and are useful for raising HDL-cholesterol, reducing LDL-cholesterol, and for treating or preventing atherosclerosis. In formula I, A-B is an arylamide moiety.

13 Claims, No Drawings

CETP INHIBITORS DERIVED FROM BENZOXAZOLE ARYLAMIDES

CROSS REFERENCE TO RELATED APPLICATIONS

This application is a U.S. National Phase application under 35 U.S.C. §371 of PCT Application No. PCT/US2008/007471, filed 16 Jun. 2008, which claims priority under 35 U.S.C. §119(e) from U.S. Application No. 60/936,534, filed 20 Jun. 2007.

FIELD OF THE INVENTION

This invention relates to a class of chemical compounds that inhibit cholesterol ester transfer protein (CETP) and therefore have utility in raising HDL-cholesterol, lowering LDL-cholesterol, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S. and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Clinical trials of Pfizer's CETP inhibitor torcetrapib were recently terminated because of increased mortality in patients who were using the drug during outcomes studies. New compounds are needed so that one or more pharmaceutical compounds can be found that are safe and effective. The novel compounds described herein are very potent CETP inhibitors. They are amide derivatives of 2-arylbenzoxazoles and related compounds. A different family of CETP inhibitors based on 2-arylbenzoxazoles is disclosed in WO 2007/070173.

SUMMARY OF THE INVENTION

Compounds having Formula I, including pharmaceutically acceptable salts of the compounds, are CETP inhibitors, and have utility in raising HDL-cholesterol, lowering LDL-cholesterol, and in treating, preventing, and/or reducing the risk of developing atherosclerosis:

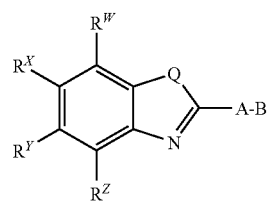

I

In the compounds of Formula I, Q is selected from the group consisting of O, S, and —N($R^2$)—;

A is a difunctional cyclic group selected from 1,4-phenylene, 2,5-pyridinylene, and 2,5-pyrimidinylene, wherein A is optionally substituted with 1-3 substituent groups $R^1$;

Each $R^1$ is independently selected from the group consisting of halogen, $C_1$-$C_3$alkyl, $C_2$-$C_3$alkenyl, $C_2$-$C_3$alkynyl, and —$OC_1$-$C_3$alkyl, wherein each alkyl, alkenyl, and alkynyl substituent is optionally substituted with 1-5 halogens;

Each $R^2$ is independently selected from the group consisting of H, $C_1$-$C_3$alkyl, $C_2$-$C_3$alkenyl, and $C_2$-$C_3$alkynyl, wherein each alkyl, alkenyl, and alkynyl substituent is optionally substituted with 1-5 halogens;

$R^W$ is selected from the group consisting of (a) $C_1$-$C_5$alkyl which is optionally substituted with 1-5 halogens, (b) $C_{2-5}$ alkenyl which is optionally substituted with 1-5 halogens; (c) —$OC_1$-$C_5$ alkyl which is optionally substituted with 1-5 halogens, (d) —$SC_1$-$C_5$ alkyl which is optionally substituted with 1-5 halogens, (e) —$OC_{2-5}$ alkenyl which is optionally substituted with 1-5 halogens, (f) $C_3$-$C_6$cycloalkyl, (g) phenyl, (h) a 5-6 membered saturated or partly unsaturated heterocyclic group having 1-3 heteroatoms independently selected from N, S and O, (i) a 5-7 membered heteroaromatic group having 1-3 heteroatoms independently selected from N, S, and O, (j) —C(=O)$OC_{1-3}$alkyl which is optionally substituted with 1-5 halogens, and (k) —C(=O)OH, wherein said $C_3$-$C_6$cycloalkyl, phenyl, 5-6 membered saturated or partly unsaturated heterocyclic group, and 5-7 membered heteroaromatic group are optionally substituted with 1-3 substituents independently selected from halogen, $CH_3$, $CF_3$, —$OCH_3$, and —$OCF_3$;

$R^Y$ is selected from the group consisting of halogen, $CH_3$, $CF_3$, —$OCH_3$, —$OCF_3$, —CN, phenyl, and a 6-membered heteroaroaromatic group having 1-2 N, wherein phenyl and the 6-membered heteroaroaromatic group are optionally substituted with 1-3 substituents independently selected from halogen, $CH_3$, $CF_3$, —$OCH_3$, and —$OCF_3$;

$R^X$ and $R^Z$ are each selected from the group consisting of H, halogen, $CH_3$, $CF_3$, —$OCH_3$, and —$OCF_3$;

B is —C(=O)N($R^3$)($CR^4R^5$)$_x$($CR^6R^7$)$_y$$D^2$;

$R^3$ is selected from the group consisting of H and $C_1$-$C_3$alkyl;

$R^4$ is selected from the group consisting of H, $C_1$-$C_3$alkyl, $CF_3$, —C(=O)OH, and —C(=O)$OC_1$-$C_3$alkyl;

$R^5$ is selected from the group consisting of H, $C_1$-$C_3$alkyl, and $CF_3$;

$R^6$ is selected from the group consisting of H, $C_1$-$C_3$alkyl, $CF_3$, —C(=O)OH, and —C(=O)$OC_1$-$C_3$alkyl;

$R^7$ is selected from the group consisting of H, $C_1$-$C_3$alkyl, $CF_3$, and phenyl, which is optionally substituted with 1-3 groups independently selected from halogen, $CH_3$, $CF_3$, —$OCH_3$, and —$OCF_3$;

x is 0 or 1;

y is 0, 1, or 2;

$D^2$ is a cyclic group selected from (a) 5-membered saturated and partly unsaturated heterocyclic groups, wherein $D^2$ comprises one ring member —N($R^8$)—, optionally 1-2 ring members independently selected from —O— and —S—, optionally one carbonyl group, and optionally 1-2 double bonds, wherein $D^2$ is optionally fused to a phenyl ring or to a $C_5$-$C_7$Cycloalkyl, wherein $D^2$ is connected to the remainder of the structure represented by Formula I through a carbon atom of $D^2$, wherein $D^2$ is optionally substituted with 1-3 substituents independently selected from halogen, —CN, —$NO_2$, —N($R^3$)$_2$—, $C_1$-$C_3$alkyl, $CF_3$, —$OCH_3$, phenyl, pyridyl, and —$OCF_3$, and optionally with 1 group $C_1$-$C_5$alkylene-phenyl, wherein phenyl and pyridyl in all uses are optionally substituted with 1-3 substituent groups independently selected from halogen, $CH_3$, $CF_3$, —$OCH_3$, and —$OCF_3$;

$R^8$ is selected from the group consisting of $C_1$-$C_9$alkyl, —C(=O)$OC_1$-$C_9$alkyl, —C(=O)$C_1$-$C_9$alkyl, —S(O)$_x$$C_1$-$C_9$alkyl, —C(=O)N($R^9$)$_2$, —$C_1$-$C_3$alkylene-C(=O)$OC_1$-$C_6$ alkyl, —$C_1$-$C_5$alkylene-$OC_1$-$C_9$alkyl, and a cyclic group $D^4$ bonded to the N to which $R^8$ is connected or to a difunctional linking group $L^4$ which is bonded to the N to which $R^8$ is connected, wherein the $C_1$-$C_9$alkyl and $C_1$-$C_6$alkyl groups in all uses are optionally substituted with 1-9 halogens;

Wherein $D^4$ is selected from the group consisting of (a) phenyl, (b) naphthyl, (c) $C_3$-$C_8$cycloalkyl optionally having 1-2 double bonds, (d) a saturated or partially unsaturated monocyclic or bicyclic 4-10 membered heterocycle having 1-3 heteroatoms independently selected from N, O, and S and optionally one —C(=O)— group, said heterocycle optionally having 1-2 double bonds, and (e) a monocyclic or bicyclic 5-12 membered heteroaromatic group having 1-3 heteroatoms independently selected from N, S, and O and optionally having one —C(=O)— group;

$L^4$ is selected from the group consisting of —C(=O)—, —C(=O)O—, —S(O)$_2$—, —C(=O)N($R^3$)—, —S(O)$_2$N($R^3$)—, —$C_1$-$C_7$alkylene-, —C(=O)$C_1$-$C_7$alkylene-, —C(=O)$C_1$-$C_7$alkyleneN($R^3$)—, —C(=O)$OC_1$-$C_7$alkylene-, —S(O)$_2$$C_1$-$C_7$alkylene-, —C(=O)N($R^3$)$C_1$-$C_7$alkylene-, —S(O)$_2$N($R^3$)$C_1$-$C_7$alkylene-, —$C_1$-$C_7$alkylene N($R^3$)S(O)$_2$—, —$C_1$-$C_7$alkylene S(O)$_2$N($R^3$)—, —$C_1$-$C_7$alkylene N($R^3$)C(=O)—, and —$C_1$-$C_7$alkylene C(=O)N($R^3$)—, wherein —$C_1$-$C_7$alkylene- optionally comprises a double bond between two adjacent carbons and optionally comprises a difunctional group selected from O, S, —S(O)$_2$—, —$NR^3$—, —C(=O)—, —N($R^3$)C(=O)—, and —N($R^3$)S(O)$_2$— between two adjacent carbons, wherein $D^4$ is optionally substituted with 1-3 substituents independently selected from halogen, —CN, —$NO_2$, —OH, $C_1$-$C_7$alkyl, $C_2$-$C_7$alkenyl, $CF_3$, —$OC_1$-$C_5$alkyl, —$C_1$-$C_5$alkylene-$OC_1$-$C_5$alkyl, —$OCF_3$, —N($R^3$)$_2$—, —C(=O)OH, and —C(=O)$OC_1$-$C_7$alkyl, and is optionally substituted with one cyclic group $D^6$ bonded directly to $D^4$ or connected to $D^4$ through a linking group $L^6$, wherein $D^6$ has the same selections as $D^4$, and $L^6$ has the same selections as $L^4$, and D6 is optionally substituted with 1-3 substituents independently selected from halogen, —CN, —$NO_2$, —OH, $C_1$-$C_7$alkyl, $C_2$-$C_7$alkenyl, $CF_3$, —$OC_1$-$C_5$alkyl, —$C_1$-$C_5$alkylene-$OC_1$-$C_5$alkyl, —$OCF_3$, —N($R^3$)$_2$—, —C(=O)OH, and —C(=O)$OC_1$-$C_7$alkyl, wherein the $C_1$-$C_7$alkyl, $C_2$-$C_7$alkenyl, and —$OC_1$-$C_5$alkyl groups in all uses in substituents on D4 and D6 are optionally substituted with 1-5 halogens; and Each $R^9$ is independently selected from the group consisting of H, $C_1$-$C_7$alkyl, $C_2$-$C_7$alkenyl, and $C_2$-$C_7$alkynyl, wherein said $C_1$-$C_7$alkyl, $C_2$-$C_7$alkenyl, and $C_2$-$C_7$alkynyl are optionally substituted with 1-9 halogens.

In the compounds of formula I and in compounds described subsequently, alkyl, alkenyl and alkynyl groups can be linear or branched, unless otherwise stated.

DETAILED DESCRIPTION OF THE INVENTION

In embodiments of the invention, the compound of Formula I has formula Ia:

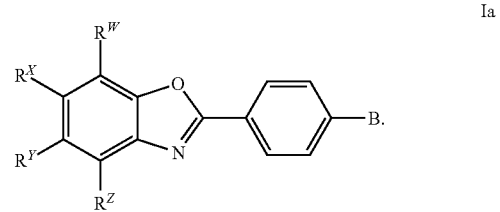

Ia

In embodiments, $R^W$ is selected from the group consisting of (a) $C_1$-$C_5$alkyl which is optionally substituted with 1-5 F, (b) $C_{2-3}$ alkenyl which is optionally substituted with 1-3 F, (c) —$OC_1$-$C_3$ alkyl which is optionally substituted with 1-3 F, (d) —$SC_1$-$C_3$ alkyl which is optionally substituted with 1-3 F, (e) —$OC_{2-3}$ alkenyl which is optionally substituted with 1-3 F, (f) $C_3$-$C_6$cycloalkyl, (g) phenyl, (h) pyridyl, (i) —C(=O)$OC_{1-3}$alkyl which is optionally substituted with 1-3 F, and (k) —C(=O)OH, wherein said $C_3$-$C_6$cycloalkyl, phenyl, and pyridinyl substituents are optionally substituted with 1-3 substituents independently selected from halogen, $CH_3$, $CF_3$, —$OCH_3$, and —$OCF_3$.

In embodiments, $R^Y$ is selected from the group consisting of halogen, $CH_3$, $CF_3$, —$OCH_3$, —$OCF_3$, and —CN.

In embodiments, $R^X$ and $R^Z$ are each selected the group consisting of H, halogen, $CH_3$, $CF_3$, —$OCH_3$, and —$OCF_3$.

In embodiments, the compound has formula Ib, including pharmaceutically acceptable salts thereof:

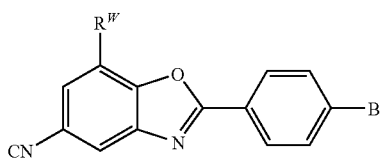

Ib

In subsets of the compounds described above, $R^W$ is selected from the group consisting of $C_1$-$C_4$alkyl which is optionally substituted with 1-3 F, $C_{2-3}$ alkenyl, —$OCH_3$, —$OCF_3$, —$SCH_3$, —$SCF_3$, cyclopropyl,)-C(=O)$OC_{1-3}$alkyl, and phenyl which is optionally substituted with 1-3 substituents independently selected from halogen, $CH_3$, $CF_3$, —$OCH_3$, and —$OCF_3$.

In subsets of the compounds described above, $D^2$ is a cyclic group selected from 1,3-oxazolidin-2-one and pyrrolidine.

In subsets of the compounds described above,
$R^3$ is selected from H and $CH_3$;
$R^4$ and $R^5$ are H;
X is 1; and
Y is 0.

In embodiments of the compounds described above, including pharmaceutically acceptable salts, $R^W$ is isopropyl.

In embodiments of the compounds described above, including pharmaceutically acceptable salts, $D^2$ is selected from 1,3-oxazolidin-2-one and pyrrolidine, and is optionally substituted with 1-2 $CH_3$ groups and optionally one phenyl group, wherein phenyl is optionally substituted with 1-3 groups independently selected from F, Cl, $CH_3$, $CF_3$, —$OCH_3$ and —$OCF_3$, and $R^8$ is attached to the N of $D^2$.

In embodiments of the compounds described above, including pharmaceutically acceptable salts, $R^8$ is selected from the group consisting of H, $C_1$-$C_3$alkyl, pyridyl, pyrimidinyl, —$CH_2$-phenyl, —$CH_2$-anthraquinone, and —$CH_2$-tetralin, wherein the non-aromatic portion of the tetralin ring is optionally substituted with 1-4 $CH_3$ groups, wherein the pyridyl, pyrimidinyl, and phenyl rings of $R^8$ are optionally substituted with 1-2 substituents independently selected from F, Cl, Br, $C_1$-$C_4$alkyl, $CF_3$, —$OC_1$-$C_4$alkyl, —$OCF_3$, $C_2$-$C_5$alkenyl, —$NO_2$, —NHC(=O)$C_1$-$C_5$alkyl, and —NHC(=O)$CH_2CO_2C_1$-$C_3$alkyl, and are optionally substituted with one cyclic group $D^6$, which is connected directly to the aromatic ring of $R^8$ or is connected to the aromatic ring of $R^8$ through a linking group $L^6$,
with the proviso that if $R^8$ is H or $C_1$-$C_3$alkyl, then $D^2$ is substituted with one phenyl group which is optionally substituted with 1-3 groups independently selected from F, Cl, $CH_3$, $CF_3$, —$OCH_3$ and —$OCF_3$, and $D^2$ is optionally also substituted with one $CH_3$ group.

In embodiments of the compounds described above, including pharmaceutically acceptable salts, $D^6$ is selected from the group consisting of phenyl, pyridyl, $C_5$-$C_6$cycloalkyl, $C_5$-$C_6$cycloalkenyl, thienyl, pyrazolyl, oxazolyl, and isoxazolyl, wherein $D^6$ is optionally substituted with 1-3 substituent groups independently selected from halogen, $C_1$-$C_5$alkyl, —$OC_1$-$C_5$alkyl, $CF_3$, —$OCF_3$, —$CO_2H$, —C(=O)$NH_2$, —NHC(=O)$C_1$-$C_5$alkyl, —$CO_2C_1$-$C_3$alkyl, —CN, —OH, —$NO_2$, —$CH_2OC_1$-$C_2$alkyl, and optionally one cyclic group selected from 1,3-dioxolanyl, thienyl, pyrazolyl, isoxazolyl, and phenyl, wherein the cyclic group is optionally substituted with 1-2 groups independently selected from $CH_3$, —$OCH_3$, $CF_3$, —$OCF_3$, and halogen; and
the optional linking group $L^6$ is selected from the difunctional groups —$C_2$-$C_4$alkenylene- and —NHC(=O)—.

In embodiments, the compounds described herein, pharmaceutically acceptable salts thereof, have formula Ic:

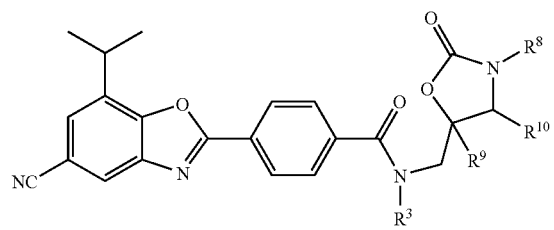

Ic wherein $R^3$ and $R^9$ are independently selected from H and $CH_3$;
$R^8$ is H or $CH_3$; and
$R^{10}$ is phenyl, which is optionally substituted with 1-2 groups independently selected from F, Cl, $CH_3$, $CF_3$, —$OCH_3$, and —$OCF_3$—.

In embodiments, the compounds described herein, and pharmaceutically acceptable salts thereof, have formula Ic:

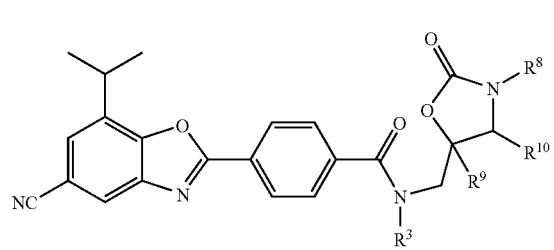

Ic wherein $R^3$ and $R^9$ are independently selected from H and $CH_3$;
$R^{10}$ is H;
$R^8$ is selected from the group consisting of pyridyl, pyrimidinyl, and —$CH_2$-phenyl, wherein the pyridyl, pyrimidinyl, and phenyl rings of $R^8$ are optionally substituted with 1-2 substituents independently selected from F, Cl, Br, $C_1$-$C_4$alkyl, $CF_3$, —$OC_1$-$C_4$alkyl, —$OCF_3$, $C_2$-$C_5$alkenyl, —$NO_2$, —NHC(=O)$C_1$-$C_5$alkyl, and —NHC(=O)$CH_2CO_2C_1$-$C_3$alkyl, and are optionally substituted with one cyclic group $D^6$, which is connected directly to the pyridyl, pyrimidinyl or phenyl ring of $R^8$ or is connected to the pyridyl, pyrimidinyl or phenyl ring of $R^8$ through a linking group $L^6$;

wherein $D^6$ is selected from the group consisting of phenyl, pyridyl, $C_5$-$C_6$cycloalkyl, $C_5$-$C_6$cycloalkenyl, thienyl, pyrazolyl, oxazolyl, and isoxazolyl, wherein $D^6$ is optionally substituted with 1-3 substituent groups independently selected from halogen, $C_1$-$C_5$alkyl, —$OC_1$-$C_5$alkyl, $CF_3$, —$OCF_3$, —$CO_2H$, —C(=O)$NH_2$, —NHC(=O)$C_1$-$C_5$alkyl, —$CO_2C_1$-$C_3$alkyl, —CN, —OH, —$NO_2$, —$CH_2OC_1$-$C_2$alkyl, and optionally one cyclic group selected from 1,3-dioxolanyl, thienyl, pyrazolyl, isoxazolyl, and phenyl, wherein the cyclic group is optionally substituted with 1-2 groups independently selected from $CH_3$, —$OCH_3$, $CF_3$, —$OCF_3$, and halogen; and wherein the optional linking group $L^6$ is selected from the difunctional groups —$C_2$-$C_4$alkenylene- and —NHC(=O)—.

The definitions of $R^8$, $D^6$, and $L^6$ provided immediately above also may be used in the description of the compounds having formula I, Ia, and Ib.

In the embodiments of the invention described above, the definition of each substituent group may be varied independently of the other groups.

Definitions

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like.

"Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 1-4 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of stereoisomers. When structures are shown without a stereochemical representation, all stereochemical structures are included individually and collectively, such as enantiomers, diastereomers (where diastereomers are possible), and mixtures of the enantiomers and/or diastereomers, including racemic mixtures. When a stereochemical structure of a compound is provided, any reference to stereoisomers includes other enantiomers, diastereomers (when possible), and mixtures of these, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. The compounds are also effective in lowering LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerostic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\square_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6, Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone βagonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2

(acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP ASSAY

An in vitro continuous assay for determining $IC_{50}$'s to identify compounds that are CETP inhibitors was performed based on a modification of the method described by Epps et al. employing BODIPY®-CE as the cholesteryl ester lipid donor and BODIPY®-TG as the triglyceride lipid donor. See Epps et al. (1995) *Method for measuring the activities of cholesteryl ester transfer protein (lipid transfer protein)*, Chem. Phys. Lipids. 77, 51-63.

Particles used in the assay were created from the following materials by probe sonication essentially as described by Epps et al. Synthetic cholesteryl ester (CE) donor HDL particles contained DOPC (Dioleoyl Phosphatidyl Choline), BODIPY®-CE (Molecular Probes C-3927), triolein (a triglyceride), dabcyl dicetylamide, (a non-diffusable quencher molecule to reduce background fluorescence) and apoHDL. Synthetic triglyceride (TG) donor HDL particles contained DOPC, BODIPY®-TG, and apoHDL. BODIPY®-TG was synthesized at room temperature from diolein and the BODIPY containing fatty acid analog 4,4-difluoro-5-(2-thienyl)-4-bora-3a,4a-diaza-s-indacene-3-dodecanoic acid (Molecular Probes) in methylene chloride in the presence of dicyclohexyl carbodimide. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), 3% human serum, and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed in a final volume of 150 μL. CE transfer reactions were performed as follows: final concentrations of materials were: 2.5 ng/μL CE donor particles, 7.5 ng/μL acceptor particles (each expressed by protein content), 1×CETP buffer, 14-30 nM recombinant human CETP (expressed in CHO cells and partially purified), and up to 2% DMSO when testing compounds; reactions were followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well. TG transfer reactions were performed as described above with the exception that 2.5 ng/uL TG donor particles were used. TG transfer was measured at an excitation wavelength of 538 nm while reading emission at 568 nm every 45 sec for 45 min at 37° C. with a cutoff filter at 550 nm.

Data were evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an $IC_{50}$ value as measured for the CE transfer reaction as described above of less than or equal to 83 μM. $IC_{50}$ values are in the range of 18 nM to 83 μM. Most of the compounds have an $IC_{50}$ value of 18 nM-200 nM, and the preferred compounds generally have $IC_{50}$ values of 18 nM-100 nM.

The compounds of Examples 2, 7, 30, 31, 43, 48, 51, 53, 54, and 55, or a stereoisomer of the compounds, have IC$_{50}$ values in the range of 18 nM-100 nM.

INTERMEDIATE 1

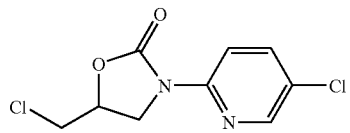

5-(Chloromethyl)-3-(5-chloropyridin-2-yl)-1,3-oxazolidin-2-one

A mixture of 5-(chloromethyl)-1,3-oxazolidin-2-one (136 mg), 2-bromo-5-chloropyridine (192 mg), cesium carbonate (489 mg), bispalladium tribenzylideneacetone (137 mg) and (9,9-dimethyl-9H-xanthene-4,5-diyl)bis(diphenylphosphine) (260 mg) in 1 ml of dioxane was stirred at 85° C. for 12 h. The sample was then cooled to room temperature, and filtered through a plug of silica gel (5×10 ml) eluting with ethyl acetate (50 ml). The eluent was concentrated in vacuo to provide a clear reddish-brown liquid, which was purified via column chromatography on a Biotage Horizon 40M column eluting with 0% ethyl acetate in hexanes (1 column volume), followed by a gradient to 100% ethyl acetate in hexanes (over 10 column volumes), and held at 100% ethyl acetate for 4 column volumes to provide the title compound (204 mg, 83%). Mass spectrum (ESI) 249.0 (M+2). 1H NMR (500 MHz, CDCl3): δ 8.28 (d, J=2.5 Hz, 1H), 8.20 (d, J=8.9 Hz, 1H), 7.68 (dd, J=9.0, 2.6 Hz, 1H), 4.90 (m, 1H), 4.35 (dd, J=8.9, 11.0 Hz, 1H), 4.17 (dd, J=5.7, 10.8 Hz, 1H), 3.78 (m, 2H).

INTERMEDIATE 2

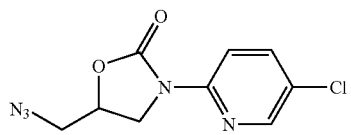

5-(Azidomethyl)-3-(5-chloropyridin-2-yl)-1,3-oxazolidin-2-one

A mixture of 5-(chloromethyl)-3-(5-chloropyridin-2-yl)-1,3-oxazolidin-2-one (204 mg, INTERMEDIATE 1) and sodium azide (107 mg) was heated to 100° C. in 10 ml of dimethylformamide for 15 h. The sample was then diluted with 100 ml of water and extracted with 100 ml of ethyl acetate (3×). The combined organic layers were washed with water (100 ml) and brine (100 ml). They were then dried over sodium sulfate and concentrated in vacuo to provide 139 mg (67%) of the title compound in >95% purity via LC/MS. Mass spectrum (ESI) 254.0 (M+1).

INTERMEDIATE 3

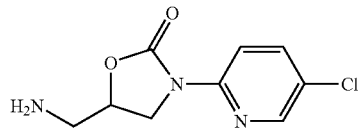

5-(Aminomethyl)-3-(5-chloropyridin-2-yl)-1,3-oxazolidin-2-one

A mixture of 5-(azidomethyl)-3-(5-chloropyridin-2-yl)-1,3-oxazolidin-2-one (139 mg, INTERMEDIATE 2) and triphenylphosphine (226 mg) was heated to 65° C. for 8 h in 66 ml of tetrahydrofuran and 9 ml of water. The sample was then cooled to room temperature, and concentrated in vacuo. The residue was purified via column chromatography on a Biotage Horizon 40M column eluting with 100% ethyl acetate (5 column volumes) to remove excess triphenylphosphine and triphenylphosphine oxide, followed by 100% methanol (5 column volumes), to provide the title compound (122 mg, 94%). Mass spectrum (ESI) 228.0 (M+1).

Example 1

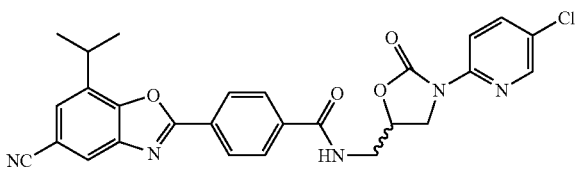

N-{[3-(5-chloropyridin-2-yl)-2-oxo-1,3-oxazolidin-5-yl]methyl}-4-(5-cyano-7-isopropyl-1,3-benzoxazol-2-yl)benzamide To 4-(5-cyano-7-isopropyl-1,3-benzoxazol-2-yl)benzoic acid (164 mg, INTERMEDIATE 36) in 20 ml of dichloromethane was added oxalyl chloride (402 μl, 2M in CH2Cl2) followed by dimethylformamide (30 μl). The mixture was allowed to stir for 1 h. LC/MS analysis shows complete consumption of starting material to form the acyl chloride. The mixture was concentrated in vacuo (with minimal or no heating (<30° C.). To this residue was then added 30 ml of dichloromethane, 5-(aminomethyl)-3-(5-chloropyridin-2-yl)-1,3-oxazolidin-2-one (122 mg), and N-ethyl-N-isopropylpropan-2-amine (559 μl). The mixture was stirred at room temperature for 15 min and subsequently purified via column chromatography on a Biotage Horizon 65i column, eluting with a gradient from 0-100% ethyl acetate in hexanes (10 column volumes). Some of the product was insoluble upon loading the mixture onto the column. This residue was scraped off the top of the column, transferred to a flask, and dried in vacuo. This sample was determined pure and combined with the chromatographed product to furnish 233 mg (84%) of the title compound as an off-white solid. Mass spectrum (ESI) 516.1 (M+1). 1H NMR (500 MHz, CDCl3): δ 8.33 (d, J=8.0 Hz, 2H), 8.27 (s, 1H), 8.16 (d, J=8.9 Hz, 1H), 7.97 (d, J=8.0 Hz, 1H), 7.94 (s, 1H), 7.67 (d, J=9.0 Hz, 1H), 7.50

(s, 1H), 6.77 (bs, 1H), 4.95 (m, 1H), 4.39 (d, J=9.7 Hz, 1H), 4.09 (m, 2H), 3.72 (m, 1H), 3.47 (m, 1H), 1.46 (d, J=6.8 Hz, 6H).

Example 2

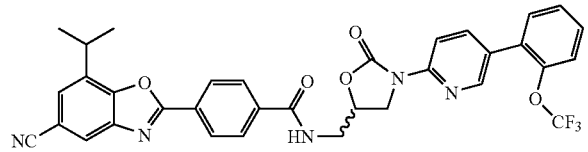

4-(5-Cyano-7-isopropyl-1,3-benzoxazol-2-yl)-N-[(2-oxo-3-{5-[2-(trifluoromethoxy)phenyl]pyridin-2-yl}-1,3-oxazolidin-5-yl)methyl]benzamide To a mixture of N-{[3-(5-chloropyridin-2-yl)-2-oxo-1,3-oxazolidin-5-yl]methyl}-4-(5-cyano-7-isopropyl-1,3-benzoxazol-2-yl)benzamide (52 mg) and potassium carbonate (55 mg) in 1 ml of tetrahydrofuran and 1 ml of water was added 2-trifluoromethoxyphenylboronic acid (82 mg) and palladium di-tert-butylphosphinoferrocene (13 mg). The mixture was heated via microwave for 15 min at 150° C. The sample was cooled to room temperature, and purified was purified via column chromatography on a Biotage Horizon 40M column eluting with 0% ethyl acetate in hexanes (1 column volumes), followed by a gradient to 100% ethyl acetate in hexanes (over 10 column volumes), and held at 100% ethyl acetate for 3 column volumes to provide the title compound as an off-white solid (53 mg, 83%). Mass spectrum (ESI) 642.2 (M+1). 1H NMR (500 MHz, CDCl3): δ 8.43 (s, 1H), 8.35 (d, J=7.8 Hz, 2H), 8.28 (d, J=8.7 Hz, 1H), 7.98 (d, J=8.3 Hz, 2H), 7.94 (s, 1H), 7.84 (d, J=8.7 Hz, 1H), 7.52 (s, 1H), 7.40 (m, 4H), 6.76 (bs, 1H), 4.98 (m, 1H), 4.48 (dd, J=9.1 Hz, 10.7 Hz, 1H), 4.13 (m, 2H), 3.72 (m, 1H), 3.49 (sept, J=6.9 Hz, 1H), 1.46 (d, J=7.1 Hz, 6H).

Following the procedure described in EXAMPLE 2, the compounds listed in Table 1 were prepared:

| EXAMPLE | R | MS (M + 1) |
|---|---|---|
| 3 | phenyl | 558.2 |
| 4 | isobutenyl | 522.2 |
| 5 | 2-isopropoxy-6-methoxyphenyl | 646.2 |
| 6 | 4-fluoro-2-isopropoxyphenyl | 634.2 |
| 7 | 2-isobutoxyphenyl | 630.3 |
| 8 | 2-(trifluoromethyl)phenyl | 626.2 |
| 9 | 2-isopropoxy-4-methylphenyl | 630.3 |
| 10 | 3,5-bis(trifluoromethyl)phenyl | 694.2 |
| 11 | 2-cyclohexylvinyl | 590.2 |

-continued
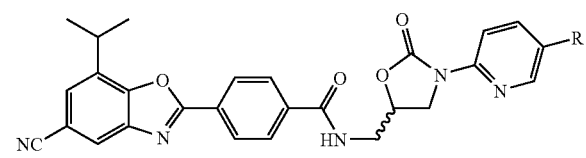
| EXAMPLE | R | MS (M + 1) |
|---|---|---|
| 12 | 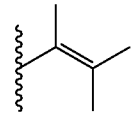 | 550.2 |
| 13 | 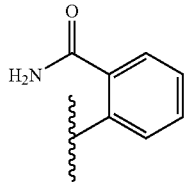 | 601.1 |
| 14 | 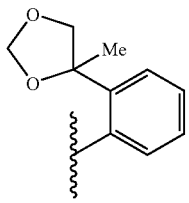 | 644.2 |
| 15 | 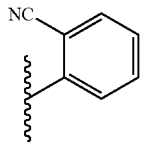 | 583.2 |
| 16 | 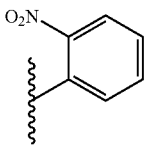 | 603.3 |
| 17 | 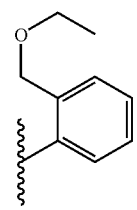 | 616.3 |
| 18 | 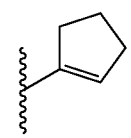 | 548.3 |
| 19 | 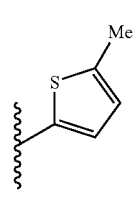 | 578.2 |
-continued
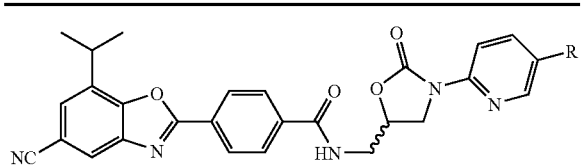
| EXAMPLE | R | MS (M + 1) |
|---|---|---|
| 20 | 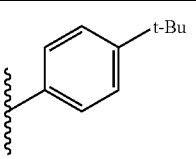 | 614.3 |
| 21 | 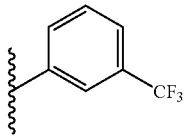 | 626.2 |
| 22 | 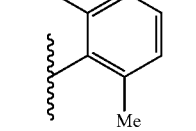 | 586.3 |
| 23 | 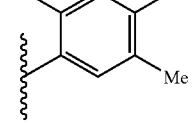 | 600.3 |
| 24 | 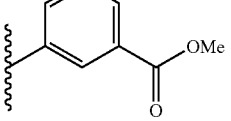 | 616.3 |
| 25 | 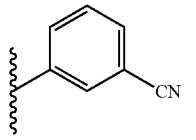 | 583.1 |
| 26 | 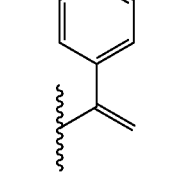 | 584.2 |

INTERMEDIATE 4

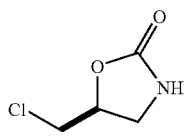

(5S)-5-(Chloromethyl)-1,3-oxazolidin-2-one

Potassium cyanate (4.38 g) was dissolved in 220 ml of water, and (S)-epichlorohydrin was slowly added (2.50 g). The solution was stirred overnight (15 h) at reflux. The reaction mixture was then extracted with ethyl acetate (while still moderately warm) (5×200 ml). The combined organic layers were dried over sodium sulfate and concentrated in vacuo to provide the title compound as a wax (which upon standing overnight in vacuo became an off-white solid) (2.18 g, 60%). Mass spectrum (ESI) 136.0 (M+1).

INTERMEDIATE 5

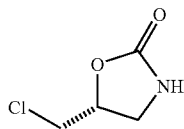

(5R)-5-(Chloromethyl)-1,3-oxazolidin-2-one

Potassium cyanate (4.38 g) was dissolved in 220 ml of water, and (R)-epichlorohydrin was slowly added (2.50 g). The solution was stirred overnight (15 h) at reflux. The reaction mixture was then extracted while still moderately warm with ethyl acetate (5×200 ml). The combined organic layers were dried over sodium sulfate and concentrated in vacuo to provide the title compound as a wax (which upon standing overnight in vacuo became an off-white solid) (2.15 g, 59%). Mass spectrum (ESI) 136.0 (M+1).

INTERMEDIATE 6

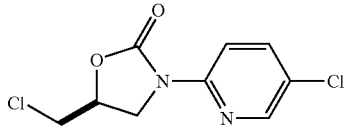

(5S)-5-(Chloromethyl)-3-(5-chloropyridin-2-yl)-1,3-oxazolidin-2-one

A mixture of (5S)-5-(chloromethyl)-1,3-oxazolidin-2-one (2.15 g, INTERMEDIATE 4), 2-bromo-5-chloropyridine (3.05 g), cesium carbonate (20.67 g), bispalladium tribenzylideneacetone (2.18 g) and (9,9-dimethyl-9H-xanthene-4,5-diyl)bis(diphenylphosphine) (2.07 g) in 16 ml of dioxane was stirred at 85° C. for 12 h. The sample was then cooled to room temperature, and purified was purified via column chromatography (2×) on a Biotage Horizon 65i column eluting with 0% ethyl acetate in hexanes (1 column volume), followed by a gradient to 60% ethyl acetate in hexanes (over 10 column volumes), and held at 60% ethyl acetate for 4 column volumes to provide the title compound (2.44 g, 61%). Mass spectrum (ESI) 249.0 (M+2).

INTERMEDIATE 7

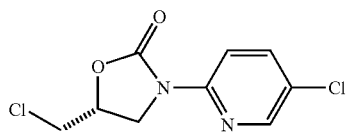

(5R)-5-(Chloromethyl)-3-(5-chloropyridin-2-yl)-1,3-oxazolidin-2-one

A mixture of (5R)-5-(chloromethyl)-1,3-oxazolidin-2-one (2.15 g, INTERMEDIATE 5), 2-bromo-5-chloropyridine (3.05 g), cesium carbonate (20.67 g), bispalladium tribenzylideneacetone (2.18 g) and (9,9-dimethyl-9H-xanthene-4,5-diyl)bis(diphenylphosphine) (2.07 g) in 16 ml of dioxane was stirred at 85° C. for 12 h. The sample was then cooled to room temperature, and purified was purified via column chromatography (2×) on a Biotage Horizon 65i column eluting with 0% ethyl acetate in hexanes (1 column volume), followed by a gradient to 60% ethyl acetate in hexanes (over 10 column volumes), and held at 60% ethyl acetate for 4 column volumes to provide the title compound (2.32 g, 59%). Mass spectrum (ESI) 249.0 (M+2).

INTERMEDIATE 8

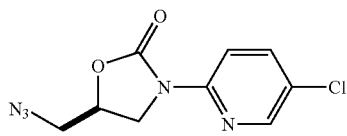

(5S)-5-(Azidomethyl)-3-(5-chloropyridin-2-yl)-1,3-oxazolidin-2-one

A mixture of (5S)-5-(chloromethyl)-3-(5-chloropyridin-2-yl)-1,3-oxazolidin-2-one (2.44 g, INTERMEDIATE 6) and sodium azide (1.28 g) was heated to 100° C. in 80 ml of dimethylformamide for 15 h. The mixture was then diluted with 500 ml of water and extracted with 500 ml of ethyl acetate (3×). The combined organic layers were washed with water (250 ml) and brine (250 ml). They were then dried over sodium sulfate and concentrated in vacuo to provide 2.31 g (92%) of the title compound in >95% purity via LC/MS. Mass spectrum (ESI) 254.1 (M+1).

INTERMEDIATE 9

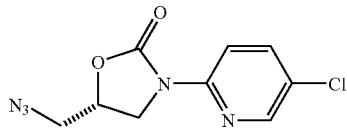

(5R)-5-(Azidomethyl)-3-(5-chloropyridin-2-yl)-1,3-oxazolidin-2-one

A mixture of (5R)-5-(chloromethyl)-3-(5-chloropyridin-2-yl)-1,3-oxazolidin-2-one (2.32 g, INTERMEDIATE 7) and sodium azide (1.22 g) was heated to 100° C. in 75 ml of dimethylformamide for 15 h. The mixture was then diluted with 500 ml of water and extracted with 500 ml of ethyl acetate (3×). The combined organic layers were washed with water (250 ml) and brine (250 ml). They were then dried over sodium sulfate and concentrated in vacuo to provide 2.22 g (93%) of the title compound in >95% purity via LC/MS. Mass spectrum (ESI) 254.1 (M+1).

INTERMEDIATE 10

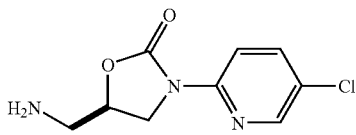

(5R)-5-(Aminomethyl)-3-(5-chloropyridin-2-yl)-1,3-oxazolidin-2-one

A mixture of (5S)-5-(azidomethyl)-3-(5-chloropyridin-2-yl)-1,3-oxazolidin-2-one (2.31 g, INTERMEDIATE 8) and triphenylphosphine (3.58 g) was heated to 65° C. for 6 h in 444 ml of tetrahydrofuran and 56 ml of water. The sample was then cooled to room temperature, and concentrated in vacuo. The residue was purified via column chromatography on a Biotage Horizon 40M column eluting with 100% ethyl acetate (5 column volumes) to remove excess triphenylphosphine and triphenylphosphine oxide, followed by 100% methanol (5 column volumes), to provide the title compound (1.70 g, 82%). Mass spectrum (ESI) 228.1 (M+1).

INTERMEDIATE 11

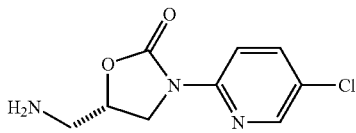

(5S)-5-(Aminomethyl)-3-(5-chloropyridin-2-yl)-1,3-oxazolidin-2-one

A mixture of (5R)-5-(azidomethyl)-3-(5-chloropyridin-2-yl)-1,3-oxazolidin-2-one (2.22 g, INTERMEDIATE 9) and triphenylphosphine (3.44 g) was heated to 65° C. for 6 h in 444 ml of tetrahydrofuran and 56 ml of water. The sample was then cooled to room temperature, and concentrated in vacuo. The residue was purified via column chromatography on a Biotage Horizon 40M column eluting with 100% ethyl acetate (5 column volumes) to remove excess triphenylphosphine and triphenylphosphine oxide, followed by 100% methanol (5 column volumes), to provide the title compound (1.74 g, 87%). Mass spectrum (ESI) 228.1 (M+1).

Example 27

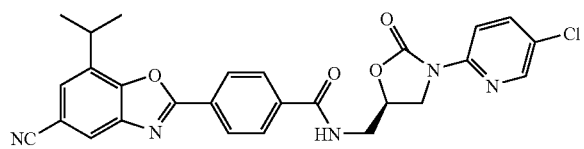

N-{[(5R)-3-(5-Chloropyridin-2-yl)-2-oxo-1,3-oxazolidin-5-yl]methyl}-4-(5-cyano-7-isopropyl-1,3-benzoxazol-2-yl)benzamide To 4-(5-cyano-7-isopropyl-1,3-benzoxazol-2-yl)benzoic acid (1.13 g, INTERMEDIATE 36) in 130 ml dichloromethane was added oxalyl chloride (2.78 ml, 2M in CH2Cl2) followed by dimethylformamide (210 µl). The mixture was allowed to stir for 1 h. LC/MS analysis shows complete consumption of starting material to form the acyl chloride. The mixture was concentrated in vacuo (with minimal or no heating (<30° C.). To this residue was then added 130 ml of dichloromethane, (5R)-5-(aminomethyl)-3-(5-chloropyridin-2-yl)-1,3-oxazolidin-2-one (1.01 g, INTERMEDIATE 10), and N-ethyl-N-isopropylpropan-2-amine (3.87 ml). The mixture was stirred at room temperature for 15 min and subsequently purified via column chromatography on a Biotage Horizon 65i column, eluting with a gradient from 0-100% ethyl acetate in hexanes (10 column volumes). Some of the product was insoluble upon loading the mixture onto the column. This residue was scraped off the top of the column, transferred to a flask, and dried in vacuo. This sample was determined pure and combined with the chromatographed product to furnish 1.52 g (79%) of the title compound as an off-white solid. Mass spectrum (ESI) 516.2 (M+1). 1H NMR (500 MHz, CDCl3): δ 8.33 (d, J=8.0 Hz, 2H), 8.27 (s, 1H), 8.16 (d, J=8.9 Hz, 1H), 7.97 (d, J=8.0 Hz, 1H), 7.94 (s, 1H), 7.67 (d, J=9.0, 1H), 7.50 (s, 1H), 6.77 (bs, 1H), 4.95 (m, 1H), 4.39 (d, J=9.7 Hz, 1H), 4.09 (m, 2H), 3.72 (m, 1H), 3.47 (m, 1H), 1.46 (d, J=6.8 Hz, 6H).

Example 28

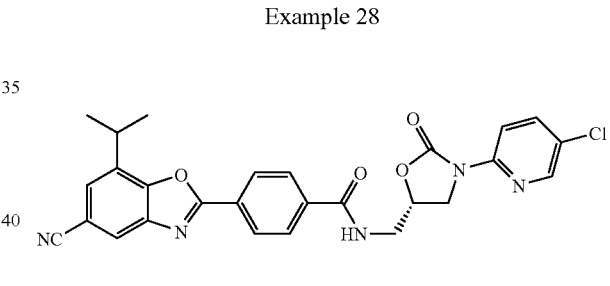

N-{[(5S)-3-(5-Chloropyridin-2-yl)-2-oxo-1,3-oxazolidin-5-yl]methyl}-4-(5-cyano-7-isopropyl-1,3-benzoxazol-2-yl)benzamide To 4-(5-cyano-7-isopropyl-1,3-benzoxazol-2-yl)benzoic acid (1.13 g, INTERMEDIATE 36) in 130 ml dichloromethane was added oxalyl chloride (2.78 ml, 2M in CH2Cl2) followed by dimethylformamide (210 µl). The mixture was allowed to stir for 1 h. LC/MS analysis shows complete consumption of starting material to form the acyl chloride. The mixture was concentrated in vacuo (with minimal or no heating (<30° C.). To this residue was then added 130 ml of dichloromethane, (5S)-5-(aminomethyl)-3-(5-chloropyridin-2-yl)-1,3-oxazolidin-2-one (1.01 g, INTERMEDIATE 11), and N-ethyl-N-isopropylpropan-2-amine (3.87 ml). The mixture was stirred at room temperature for 15 min and subsequently purified via column chromatography on a Biotage Horizon 65i column, eluting with a gradient from 0-100% ethyl acetate in hexanes (10 column volumes). Some of the product was insoluble upon loading the mixture onto the column. This residue was scraped off the top of the column, transferred to a flask, and dried in vacuo. This sample was determined pure and combined with the chromatographed product to furnish 1.48 g (78%) of the title compound as an off-white solid. Mass spectrum (ESI) 516.2 (M+1). 1H NMR (500 MHz, CDCl3): δ 8.33 (d, J=8.0 Hz, 2H), 8.27 (s, 1H), 8.16 (d, J=8.9 Hz, 1H), 7.97 (d, J=8.0 Hz, 1H), 7.94 (s, 1H), 7.67 (d, J=9.0, 1H), 7.50 (s, 1H), 6.77 (bs, 1H), 4.95 (m, 1H), 4.39 (d, J=9.7 Hz, 1H), 4.09 (m, 2H), 3.72 (m, 1H), 3.47 (m, 1H), 1.46 (d, J=6.8 Hz, 6H).

Example 29

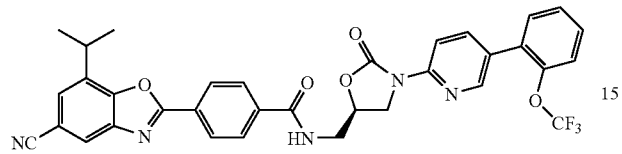

4-(5-Cyano-7-isopropyl-1,3-benzoxazol-2-yl)-N-[((5R)-2-oxo-3-{5-[2-(trifluoromethoxy)phenyl] pyridin-2-yl}-1,3-oxazolidin-5-yl)methyl]benzamide To a mixture of N-{[(5R)-3-(5-chloropyridin-2-yl)-2-oxo-1,3-oxazolidin-5-yl]methyl}-4-(5-cyano-7-isopropyl-1,3-benzoxazol-2-yl)benzamide (52 mg, EXAMPLE 27) and potassium carbonate (55 mg) in 1 ml of tetrahydrofuran and 1 ml of water was added 2-trifluoromethoxyphenylboronic acid (82 mg) and palladium di-tert-butylphosphinoferrocene (13 mg). The mixture was heated via microwave for 25 min at 150° C. The sample was cooled to room temperature, and was purified via column chromatography on a Biotage Horizon 40M column eluting with 0% ethyl acetate in hexanes (1 column volume), followed by a gradient to 100% ethyl acetate in hexanes (over 10 column volumes), and held at 100% ethyl acetate for 3 column volumes to provide the title compound as an off-white solid (39 mg, 61%). Mass spectrum (ESI) 642.3 (M+1). 1H NMR (500 MHz, CDCl3): δ 8.43 (s, 8.35 (d, J=7.8 Hz, 2H), 8.28 (d, J=8.7 Hz, 1H), 7.98 (d, J=8.3 Hz, 2H), 7.94 (s, 1H), 7.84 (d, J=8.7 Hz, 1H), 7.52 (s, 1H), 7.40 (m, 4H), 6.76 (bs, 1H), 4.98 (m, 1H), 4.48 (dd, J=9.1 Hz, 10.7 Hz, 1H), 4.13 (m, 2H), 3.72 (m, 1H), 3.49 (sept, J=6.9 Hz, 1H), 1.46 (d, J=7.1 Hz, 6H).

Following the procedure described in EXAMPLE 29, the compounds listed in Table 2 were prepared:

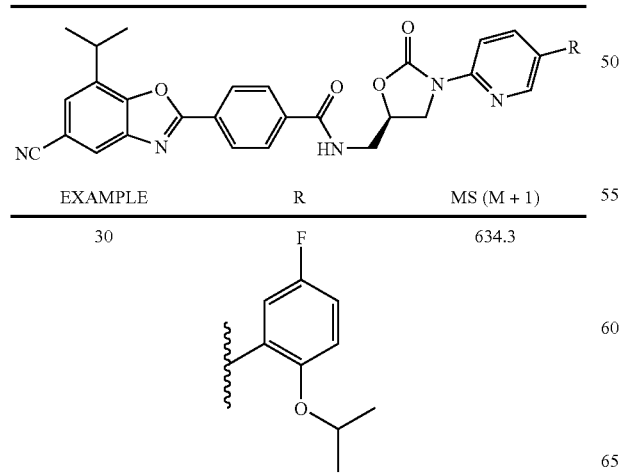

| EXAMPLE | R | MS (M + 1) |
|---|---|---|
| 30 | (2-fluoro-4-isopropoxyphenyl) | 634.3 |
| 31 | (5-isopropyl-4-fluoro-2-methoxyphenyl) | 648.3 |
| 32 | (2-methoxyphenyl) | 588.3 |
| 33 | (2,6-bis(trifluoromethyl)phenyl) | 694.0 |
| 34 | (2-isopropoxy-6-methoxyphenyl) | 646.2 |
| 35 | (2-(trifluoromethyl)phenyl) | 626.0 |
| 36 | (2-isobutoxyphenyl) | 630.2 |
| 37 | (2-fluoro-6-isopropoxyphenyl) | 634.3 |

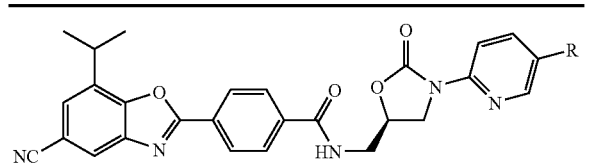

| EXAMPLE | R | MS (M + 1) |
|---|---|---|
| 38 | 2-carboxyphenyl | 602.2 |
| 39 | 2-hydroxyphenyl | 574.3 |

Example 40

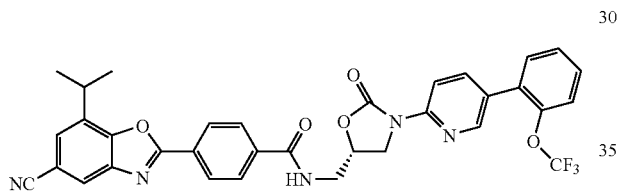

4-(5-Cyano-7-isopropyl-1,3-benzoxazol-2-yl)-N-[((5S)-2-oxo-3-{5-[2-(trifluoromethoxy)phenyl]pyridin-2-yl}-1,3-oxazolidin-5-yl)methyl]benzamide To a mixture of N-{[(5S)-3-(5-chloropyridin-2-yl)-2-oxo-1,3-oxazolidin-5-yl]methyl}-4-(5-cyano-7-isopropyl-1,3-benzoxazol-2-yl)benzamide (52 mg, EXAMPLE 28) and potassium carbonate (55 mg) in 1 ml of tetrahydrofuran and 1 ml of water was added 2-trifluoromethoxyphenylboronic acid (82 mg) and palladium di-tert-butylphosphinoferrocene (13 mg). The mixture was heated via microwave for 25 min at 150° C. The sample was cooled to room temperature, and was purified via column chromatography on a Biotage Horizon 40M column eluting with 0% ethyl acetate in hexanes (1 column volume), followed by a gradient to 100% ethyl acetate in hexanes (over 10 column volumes), and held at 100% ethyl acetate for 3 column volumes to provide the title compound as an off-white solid (41 mg, 64%). Mass spectrum (ESI) 642.3 (M+1). 1H NMR (500 MHz, CDCl3): δ 8.43 (s, 1H), 8.35 (d, J=7.8 Hz, 2H), 8.28 (d, J=8.7 Hz, 1H), 7.98 (d, J=8.3 Hz, 2H), 7.94 (s, 1H), 7.84 (d, J=8.7 Hz, 1H), 7.52 (s, 1H), 7.40 (m, 4H), 6.76 (bs, 1H), 4.98 (m, 1H), 4.48 (dd, J=9.1 Hz, 10.7 Hz, 1H), 4.13 (m, 2H), 3.72 (m, 1H), 3.49 (sept, J=6.9 Hz, 1H), 1.46 (d, J=7.1 Hz, 6H).

Following the procedure described in EXAMPLE 40, the compounds listed in Table 3 were prepared:

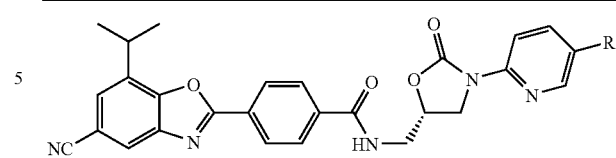

| EXAMPLE | R | MS (M + 1) |
|---|---|---|
| 41 | 2-isopropoxy-4-fluorophenyl | 634.3 |
| 42 | 2-fluoro-4-methoxy-5-isopropylphenyl | 648.4 |
| 43 | 2-methoxyphenyl | 588.3 |
| 44 | 2,6-bis(trifluoromethyl)phenyl | 694.0 |
| 45 | 2-isopropoxy-6-methoxyphenyl | 646.2 |
| 46 | 2-(trifluoromethyl)phenyl | 626.0 |
| 47 | 2-isobutoxyphenyl | 630.3 |

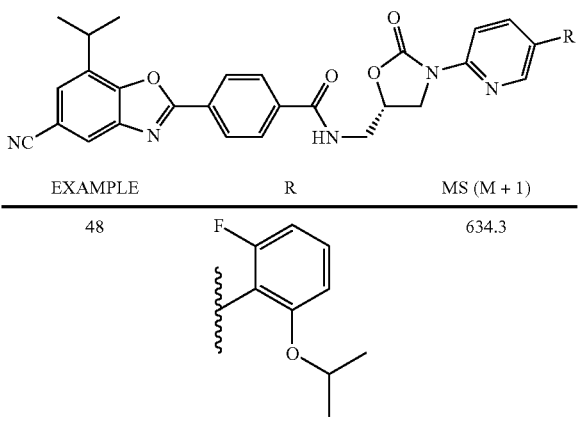

| EXAMPLE | R | MS (M + 1) |
|---|---|---|
| 48 | (2-fluoro-6-isopropoxyphenyl) | 634.3 |

INTERMEDIATE 12

(2S)-1-(Benzylamino)-3-chloropropan-2-ol

A scintillation vial was charged with benzylamine (1 g, 10 mmol), anhydrous petroleum ether (10 ml) and a stir bar. To this was added (S)-(+)-epichlorohydrin (0.925 g, 10 mmol) dropwise over a period of 20 min and the mixture was allowed to stir at room temperature. After 15 h, the white crystals precipitated from solution. These were collected by suction filtration, rinsed with cold petroleum ether (10 ml) and dried under vacuum to provide the title compound (1.0 g, 50%). Mass spectrum (ESI) 200.1 (M+1).

INTERMEDIATE 13

(5S)-3-Benzyl-5-(chloromethyl)-1,3-oxazolidin-2-one

To a 250 ml round bottom flask was added (2S)-1-(benzylamino)-3-chloropropan-2-ol (1.0 g, 5 mmol, INTERMEDIATE 12), chloroform (15 ml), and diisopropylamine (3.23 g, 25 mmol). To this was added carbonyldiimidazole (1.63 g, 10 mmol), and the mixture was heated to 45° C. for 15 h. The reaction then was diluted with dichloromethane (25 ml) and washed with water. The organic phase was dried over sodium sulfate, filtered and concentrated in vacuo to provide a pale tan residue. The product was isolated on silica gel eluting with a gradient of ethyl acetate in hexanes from 0% to 100% to provide 750 mg of product as colorless oil. Mass spectrum (ESI) 226.1 (M+1).

INTERMEDIATE 14

(5S)-5-(Azidomethyl)-3-benzyl-1,3-oxazolidin-2-one

A 40 ml vial was charged with 3-benzyl-5-(chloromethyl)-1,3-oxazolidin-2-one (112 mg, 0.5 mmol, INTERMEDIATE 13), dimethylformamide (5 ml), and sodium azide (130 mg, 2 mmol). The mixture was heated to 120° C. for 15 h. The crude was applied to a pad of silica and washed with methanol (2×10 ml). The organics were pooled and concentrated to provide a residue. The title compound was isolated on silica gel eluting with a gradient of dichloromethane/methanol from 0% to 100% to provide 100 mg (86%) as a tan oil. Mass spectrum (ESI) 233.2 (M+1).

INTERMEDIATE 15

(5R)-5-(Aminomethyl)-3-benzyl-1,3-oxazolidin-2-one

A 40 ml vial was charged with 5-(azidomethyl)-3-benzyl-1,3-oxazolidin-2-one (100 mg, 0.43 mmol, INTERMEDIATE 14), palladium on carbon (5 mg), and methanol (15 ml). The reduction was effected using a balloon filled with hydrogen at room temperature overnight. The catalyst was removed through filtration on a pad of Celite pre-rinsed with methanol. The Celite pad was further rinsed with methanol (2×5 ml) and the eluent concentrated in vacuo to provide 75 mg (85%) of the title compound. Mass spectrum (ESI) 207.2 (M+1).

Example 49

N-{[(5R)-3-Benzyl-2-oxo-1,3-oxazolidin-5-yl]methyl}-4-(5-cyano-7-isopropyl-1,3-benzoxazol-2-yl)benzamide The titled compound was prepared using a procedure analogous to that described in EXAMPLE 1. Mass spectrum (ESI) 495.2 (M+1). 1H NMR (500 MHz, CDCl3): δ 8.34 (d, J=8.4 Hz, 2H), 7.96 (s, 1H), 7.91 (d, J=8.2 Hz, 2H), 7.53 (s, 1H), 7.25 (m, 5H), 6.69 (bs, 1H), 4.76 (m, 1H), 4.41 (d, J=7.8

Hz, 2H), 3.88 (m, 1H), 3.65 (m, 1H), 3.49 (sept, J=7.0 Hz, 1H), 3.25 (m, 1H), 1.48 (d, J=7.0 Hz, 6H).

INTERMEDIATE 16

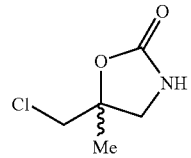

5-(Chloromethyl)-5-methyl-1,3-oxazolidin-2-one

Potassium cyanate (7.61 g) was dissolved in 350 ml of water, and 2-(chloromethyl)-2-methyloxirane was slowly added (5.00 g). The solution was stirred overnight (15 h) at reflux. The reaction mixture was then extracted while still moderately warm with ethyl acetate (5×200 ml). The combined organic layers were dried over sodium sulfate and concentrated in vacuo to provide the title compound an off-white solid (3.32 g, 47%). Mass spectrum (ESI) 150.0 (M+1). 1H NMR (500 MHz, CDCl3): δ 5.23 (bs, 1H), 3.70 (d, J=8.7 Hz, 1H), 3.68 (d, J=11.0 Hz, 1H), 3.56 (d, J=11.2 Hz, 1H), 3.34 (d, J=8.9 Hz, 1H), 1.59 (s, 3H).

INTERMEDIATE 17

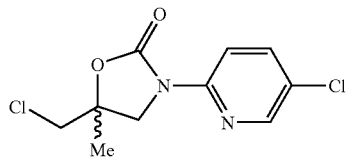

5-(Chloromethyl)-3-(5-chloropyridin-2-yl)-5-methyl-1,3-oxazolidin-2-one

A mixture of 5-(chloromethyl)-5-methyl-1,3-oxazolidin-2-one (1.50 g, INTERMEDIATE 16), 2-bromo-5-chloropyridine (1.92 g), cesium carbonate (4.89 g), bispalladium tribenzylideneacetone (1.37 g) and (9,9-dimethyl-9H-xanthene-4,5-diyl)bis(diphenylphosphine) (1.30 g) in 25 ml of dioxane was stirred at 85° C. for 12 h. The sample was then cooled to room temperature, and filtered through a plug of silica gel (15×15 ml) of silica gel eluting with ethyl acetate. The eluent then was concentrated in vacuo and purified via column chromatography on a Biotage Horizon 65i column eluting with 0% ethyl acetate in hexanes (1 column volume), followed by a gradient to 60% ethyl acetate in hexanes (over 10 column volumes), and held at 60% ethyl acetate for 4 column volumes to provide the title compound (1.01 g, 39%). Mass spectrum (ESI) 262.9 (M+2).). 1H NMR (500 MHz, CDCl3): δ 8.27 (d, J=2.5 Hz, 1), 8.21 (d, J=8.9 Hz, 1H), 7.68 (dd, J=8.9, 2.5 Hz, 1H), 4.31 (d, J=10.8 Hz, 1H), 3.95 (d, J=10.7 Hz, 1H), 3.73 (d, J=11.7 Hz, 1H), 3.63 (d, J=11.7 Hz, 1H), 1.66 (s, 3H).

INTERMEDIATE 18

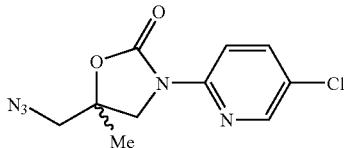

5-(Azidomethyl)-3-(5-chloropyridin-2-yl)-5-methyl-1,3-oxazolidin-2-one

A mixture of 5-(chloromethyl)-3-(5-chloropyridin-2-yl)-5-methyl-1,3-oxazolidin-2-one (1.01 g, INTERMEDIATE 17) and sodium azide (503 mg) was heated to 140° C. in 40 ml of dimethylformamide for 40 h. The mixture was then cooled to room temperature, and diluted with 150 ml of water and extracted with 150 ml of ethyl acetate (3×). The combined organic layers were washed with water (100 ml) and brine (100 ml). Then they were dried over sodium sulfate and concentrated in vacuo (overnight to remove dimethylformamide) to provide 570 mg (55%) of the title compound. Mass spectrum (ESI) 268.1 (M+1).

INTERMEDIATE 19

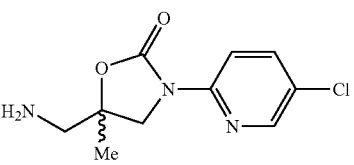

5-(Aminomethyl)-3-(5-chloropyridin-2-yl)-5-methyl-1,3-oxazolidin-2-one

A mixture of 5-(azidomethyl)-3-(5-chloropyridin-2-yl)-5-methyl-1,3-oxazolidin-2-one (570 mg, INTERMEDIATE 18) and triphenylphosphine (1.12 g) was heated to 65° C. for 4 h in 80 ml of tetrahydrofuran and 10 ml of water. The sample was then cooled to room temperature, and concentrated in vacuo. The residue was purified via column chromatography on a Biotage Horizon 40M column eluting with 100% ethyl acetate (4 column volumes) to remove excess triphenylphosphine and triphenylphosphine oxide, followed by 100% methanol (4 column volumes), to provide the title compound (457 g, 89%). Mass spectrum (ESI) 242.1 (M+1).

Example 50

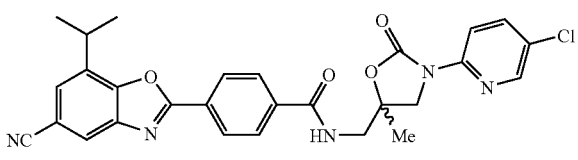

N-{[3-(5-Chloropyridin-2-yl)-5-methyl-2-oxo-1,3-oxazolidin-5-yl]methyl}-4-(5-cyano-7-isopropyl-1,3-benzoxazol-2-yl)benzamide To 4-(5-cyano-7-isopropyl-1,3-benzoxazol-2-yl)benzoic acid (579 mg, INTERMEDIATE 36) in 65 ml dichloromethane was added oxalyl chloride (1.89 ml, 2M in CH2Cl2) followed by dimethylformamide (210 µl). The mixture was allowed to stir for 1 h. LC/MS analysis shows complete consumption of starting material to form the acyl chloride. The mixture was concentrated in vacuo (with minimal or no heating (<30° C.). To this residue was then added 130 ml of dichloromethane, 5-(aminomethyl)-3-(5-chloropyridin-2-yl)-5-methyl-1,3-oxazolidin-2-one (457 g, INTERMEDIATE 19), and N-ethyl-N-isopropylpropan-2-amine (1.98 ml). The mixture was stirred at room temperature for 15 min and subsequently purified via column chromatography on a Biotage Horizon 45M column, eluting with a gradient from 0 to 100% ethyl acetate in hexanes (10 column volumes) and then held at 100% ethyl acetate (4 column volumes) to furnish the title compound as an off-white solid (603 mg, 60%). Mass spectrum (ESI) 530.2 (M+1). 1H NMR (500 MHz, CDCl3): δ 8.32 (d, J=8.2 Hz, 2H), 8.25 (d, J=2.3 Hz, 1H), 8.16 (d, J=9.2 Hz, 1H), 7.94 (s, 1H), 7.92 (d, J=8.5 Hz, 2H), 7.65 (dd, J=9.2, 2.5 Hz, 1H), 7.52 (s, 1H), 6.64 (t, J=6.3 Hz, 1H), 4.20 (d, J=10.7 Hz, 1H), 4.04 (d, J=10.8 Hz, 1H), 3.92 (dd, J=14.5, 6.3 Hz, 1H), 3.83 (dd, J=14.4, 6.4 Hz, 1H), 3.48 (sept, J=7.0 Hz, 1H), 1.63 (s, 3H), 1.46 (d, J=6.8 Hz, 6H). The enantiomers of this compound can be separated via chiral SFC on a ChiralPak AS-H column (40% isopropanol/CO2 @ 50 ml/minute) (tR first enantiomer: 2.88 min, tR second enantiomer: 3.94 min). Each enantiomer can be employed separately in the procedures described below.

Example 51

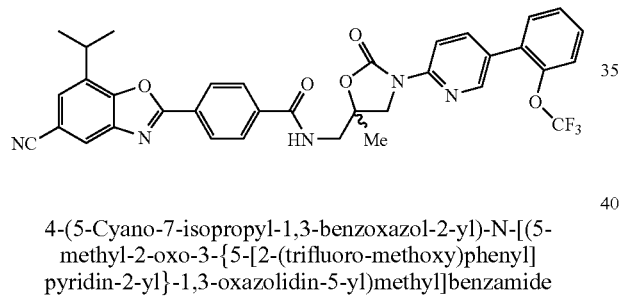

4-(5-Cyano-7-isopropyl-1,3-benzoxazol-2-yl)-N-[(5-methyl-2-oxo-3-{5-[2-(trifluoro-methoxy)phenyl]pyridin-2-yl}-1,3-oxazolidin-5-yl)methyl]benzamide To a mixture of N-{[3-(5-chloropyridin-2-yl)-5-methyl-2-oxo-1,3-oxazolidin-5-yl]methyl}-4-(5-cyano-7-isopropyl-1,3-benzoxazol-2-yl)benzamide (26 mg, EXAMPLE 50) and potassium carbonate (35 mg) in 0.5 ml of tetrahydrofuran and 0.5 ml of water was added 2-trifluoromethoxyphenylboronic acid (10 mg) and palladium di-tert-butylphosphinoferrocene (7 mg). The mixture was heated via microwave for 10 min at 100° C. The sample was cooled to room temperature, and was purified via column chromatography on a Biotage Horizon 40M column eluting with 0% ethyl acetate in hexanes (1 column volume), followed by a gradient to 100% ethyl acetate in hexanes (over 10 column volumes), and held at 100% ethyl acetate for 4 column volumes to provide the title compound as an off-white solid (8 mg, 24%). Mass spectrum (ESI) 656.4 (M+1). 1H NMR (500 MHz, CDCl3):): δ 8.40 (d, J=2.0 Hz, 1H), 8.31 (d, J=8.3 Hz, 2H), 8.25 (d, J=8.7 Hz, 1H), 7.95 (d, J=8.5 Hz, 2H), 7.92 (s, 1H), 7.82 (dd, J=8.7, 2.3 Hz, 1H), 7.51 (s, 1H), 7.40 (m, 4H), 6.82 (t, J=6.3 Hz, 1H), 4.30 (d, J=10.7 Hz, 1H), 4.13 (d, J=10.8 Hz, 1H), 3.94 (dd, J=14.5, 6.3 Hz, 1H), 3.86 (dd, J=14.5, 6.5 Hz, 1H), 3.47 (sept, J=6.9 Hz, 1H), 1.65 (s, 3H), 1.45 (d, J=6.9 Hz, 6H).

Following the procedure described in EXAMPLE 51, the compounds listed in Table 4 were prepared:

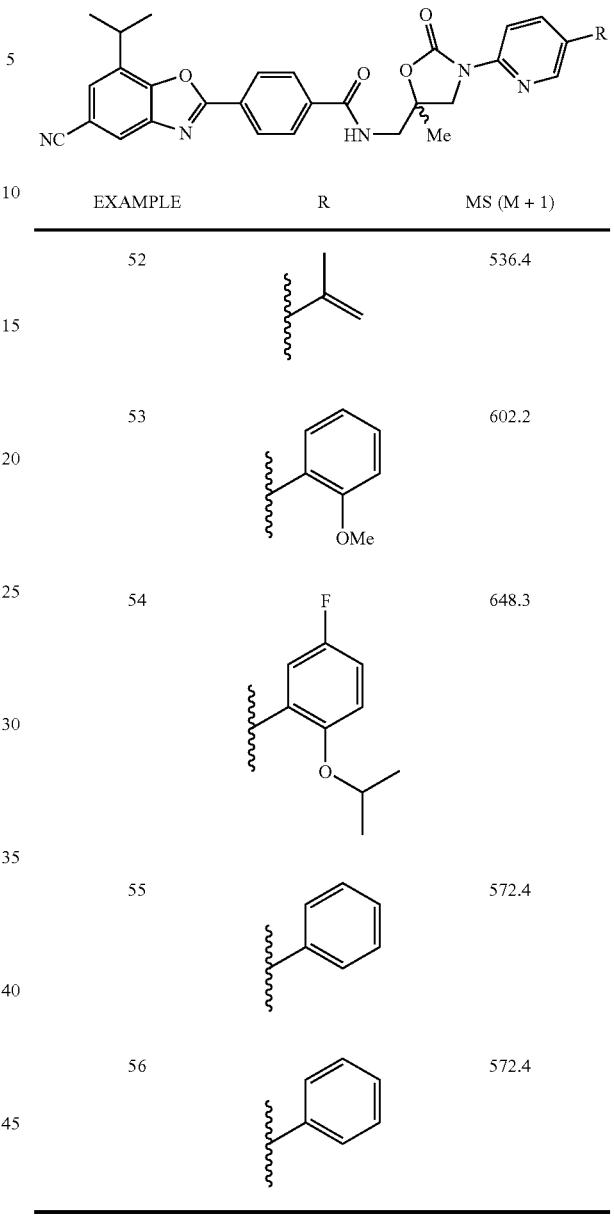

| EXAMPLE | R | MS (M + 1) |
|---|---|---|
| 52 | isobutenyl | 536.4 |
| 53 | 2-methoxyphenyl | 602.2 |
| 54 | 4-fluoro-2-isopropoxyphenyl | 648.3 |
| 55 | phenyl | 572.4 |
| 56 | phenyl | 572.4 |

INTERMEDIATE 20

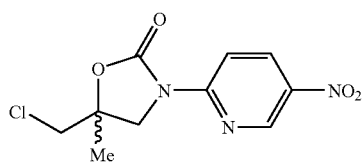

5-(Chloromethyl)-5-methyl-3-(5-nitropyridin-2-yl)-1,3-oxazolidin-2-one

The title compound was prepared in a procedure analogous to that described for INTERMEDIATE 17. Mass spectrum (ESI) 272.0 (M+1).

INTERMEDIATE 21

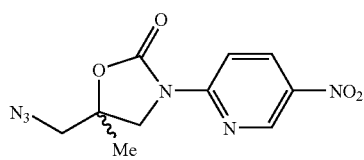

5-(Azidomethyl)-5-methyl-3-(5-nitropyridin-2-yl)-1,3-oxazolidin-2-one

The title compound was prepared in a procedure analogous to that described for INTERMEDIATE 18. Mass spectrum (ESI) 278.9 (M+1).

INTERMEDIATE 22

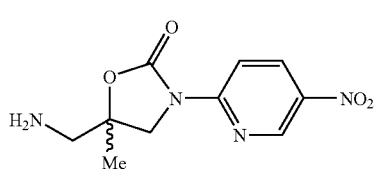

5-(Aminomethyl)-5-methyl-3-(5-nitropyridin-2-yl)-1,3-oxazolidin-2-one

The title compound was prepared in a procedure analogous to that described for INTERMEDIATE 19. Mass spectrum (ESI) 253.0 (M+1).

Example 57

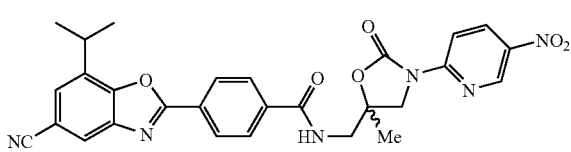

4-(5-Cyano-7-isopropyl-1,3-benzoxazol-2-yl)-N-{[5-methyl-3-(5-nitropyridin-2-yl)-2-oxo-1,3-oxazolidin-5-yl]methyl}benzamide The title compound was prepared in a procedure analogous to that described for EXAMPLE 50. Mass spectrum (ESI) 541.2 (M+1). 1H NMR (500 MHz, CDCl3): δ 9.17 (d, J=2.8 Hz, 1H), 8.46 (dd, J=9.3, 2.6 Hz, 1H), 8.39 (d, J=9.2 Hz, 1H), 8.32 (d, J=8.5 Hz, 2H), 7.94 (s, 1H), 7.92 (d, J=8.5 Hz, 2H), 7.52 (s, 1H), 6.63 (t, J=6.4 Hz, 1H), 4.32 (d, J=11.2 Hz, 1H), 4.13 (d, J=11.3 Hz, 1H), 3.98 (dd, J=14.6, 6.2 Hz, 1H), 3.82 (dd, J=14.6, 6.3 Hz, 1H), 3.48 (sept, J=7.0 Hz, 1H), 1.67 (s, 3H), 1.46 (d, J=6.9 Hz, 6H).

INTERMEDIATE 23

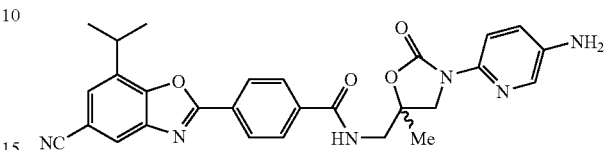

N-{[3-(5-Aminopyridin-2-yl)-5-methyl-2-oxo-1,3-oxazolidin-5-yl]methyl}-4-(5-cyano-7-isopropyl-1,3-benzoxazol-2-yl)benzamide To a mixture of 4-(5-cyano-7-isopropyl-1,3-benzoxazol-2-yl)-N-{[5-methyl-3-(5-nitropyridin-2-yl)-2-oxo-1,3-oxazolidin-5-yl]methyl}benzamide (154 mg, EXAMPLE 57) in 10 ml of methanol and 10 ml of tetrahydrofuran was added 50 mg of palladium on carbon (10% wet). The mixture was stirred at 40° C. under a balloon of hydrogen for 15 h. The sample was cooled to room temperature, and was filtered through a small plug of Celite, eluting with methanol. The eluent was concentrated and purified via column chromatography on a Biotage Horizon 40M column eluting with 0% ethyl acetate in hexanes (1 column volume), followed by a gradient to 100% ethyl acetate in hexanes (over 10 column volumes), and held at 100% ethyl acetate for 6 column volumes to provide the title compound (122 mg, 84%). Mass spectrum (ESI) 511.1 (M+1).

Example 58

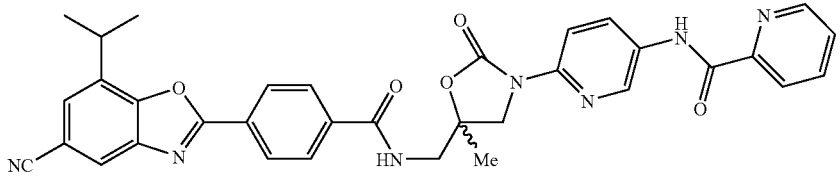

N-{6-[5-({[4-(5-Cyano-7-isopropyl-1,3-benzoxazol-2-yl)benzoyl]amino}methyl)-5-methyl-2-oxo-1,3-oxazolidin-3-yl]pyridin-3-yl}pyridine-2-carboxamide To a solution of N-{[3-(5-aminopyridin-2-yl)-5-methyl-2-oxo-1,3-oxazolidin-5-yl]methyl}-4-(5-cyano-7-isopropyl-1,3-benzoxazol-2-yl)benzamide (10 mg, INTERMEDIATE 23) and diisopropylethylamine (7 µl) in 4 ml of dichloromethane was added picolinoyl chloride (3 mg). The mixture was stirred at room temperature for 1 h. The sample was purified directly via column chromatography on a Biotage Horizon 12M column eluting with 0% ethyl acetate in hexanes (1 column volume), followed by a gradient to 100% ethyl acetate in hexanes (over 10 column volumes), and held at 100% ethyl acetate for 4 column volumes to provide the title compound (4 mg, 34%). Mass spectrum (ESI) 616.2 (M+1). 1H NMR (500 MHz, CDCl3): δ 9.01 (s, 1H), 8.69 (d, J=3.9 Hz, 1H), 8.47 (d, J=8.4 Hz, 2H), 8.33 (d, J=8.3 Hz, 2H), 8.31 (d, J=7.8 Hz, 1H), 8.16 (s, 1H), 8.08 (d, J=8.3 Hz, 2H), 7.92 (s, 1H), 7.73 (s, 1H), 7.51 (s, 1H), 7.41 (bs, 1H), 6.65 (bs, 1H), 4.94 (bs, 1H), 4.04 (d, J=10.3 Hz, 1H), 3.99 (dd, J=14.2, 6.6 Hz, 1H), 3.83 (dd, J=14.4, 6.4 Hz, 1H), 3.47 (sept, J=7.0 Hz, 1H), 1.67 (s, 3H), 1.46 (d, J=6.9 Hz, 6H).

Following the procedure described in EXAMPLE 58, the compounds listed in Table 5 were prepared:

| EXAMPLE | R | MS (M + 1) |
|---|---|---|
| 59 | 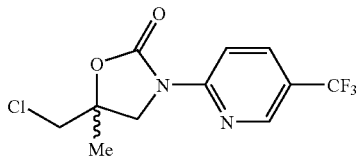 tert-butyl | 595.4 |
| 60 | isoxazolyl | 606.1 |
| 61 | methyloxazolyl | 620.2 |
| 62 | methylpyrazolyl | 633.2 |
| 63 | -CH2C(O)OEt | 564.1 |

INTERMEDIATE 24

5-(Chloromethyl)-5-methyl-3-[5-(trifluoromethyl)pyridin-2-yl]-1,3-oxazolidin-2-one The title compound was prepared in a procedure analogous to that described for INTERMEDIATE 17. Mass spectrum (ESI) 295.0 (M+1).

INTERMEDIATE 25

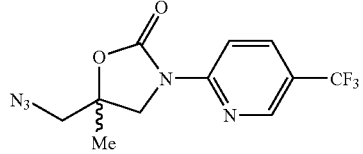

5-(Azidomethyl)-5-methyl-3-[5-(trifluoromethyl)pyridin-2-yl]-1,3-oxazolidin-2-one The title compound was prepared in a procedure analogous to that described for INTERMEDIATE 18. Mass spectrum (ESI) 301.9 (M+1).

INTERMEDIATE 26

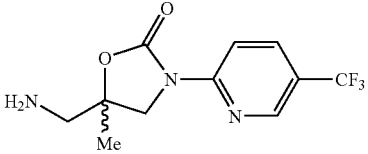

5-(Aminomethyl)-5-methyl-3-[5-(trifluoromethyl)pyridin-2-yl]-1,3-oxazolidin-2-one The title compound was prepared in a procedure analogous to that described for INTERMEDIATE 19. Mass spectrum (ESI) 276.0 (M+1).

Example 64

4-(5-Cyano-7-isopropyl-1,3-benzoxazol-2-yl)-N-({5-methyl-2-oxo-3-[5-(trifluoromethyl)pyridin-2-yl]-1,3-oxazolidin-5-yl}methyl)benzamide The title compound was prepared in a procedure analogous to that described for EXAMPLE 50. Mass spectrum (ESI) 564.1 (M+1). 1H NMR (500 MHz, CDCl3): δ 8.83 (d, J=2.6 Hz, 1H), 8.37 (dd, J=9.2, 2.5 Hz, 1H), 8.29 (d, J=9.2 Hz, 1H), 8.15 (d, J=8.3 Hz, 2H), 7.88 (s, 1H), 7.73 (d, J=8.6 Hz, 2H), 7.45 (s, 1H), 6.41 (t, J=6.7 Hz, 1H), 4.23 (d, J=11.2 Hz, 1H), 4.06 (d, J=11.2 Hz, 1H), 3.87 (dd, J=14.3, 6.2 Hz, 1H), 3.75 (dd, J=14.5, 6.2 Hz, 1H), 3.47 (sept, J=6.9 Hz, 1H), 1.67 (s, 3H), 1.46 (d, J=7.0 Hz, 6H).

INTERMEDIATE 27

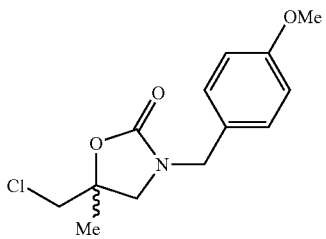

5-(Chloromethyl)-3-(4-methoxybenzyl)-5-methyl-1,3-oxazolidin-2-one

To a mixture was sodium hydride (401 mg, 60% dispersion) in 50 ml of dimethylformamide was added 5-(chloromethyl)-5-methyl-1,3-oxazolidin-2-one (1.00 g, INTERMEDIATE 16) followed by 4-methoxybenzylchloride (1.05 g). The mixture was stirred at 90° C. for 4 h. Excess sodium hydride was quenched by addition of 3 ml of methanol. The sample was then transferred to a Biotage 65i column and purified via column chromatography on a Biotage Horizon eluting with 0% ethyl acetate in hexanes (1 column volume), followed by a gradient to 50% ethyl acetate in hexanes (over 6 column volumes), and held at 50% ethyl acetate (2 column volumes) to provide the title compound (1.41 g, 78%). Mass spectrum (ESI) 271.9 (M+2).

INTERMEDIATE 28

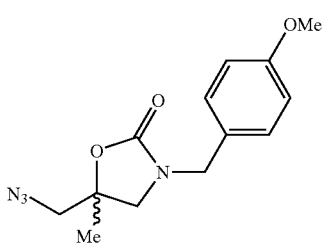

5-(Azidomethyl)-3-(4-methoxybenzyl)-5-methyl-1,3-oxazolidin-2-one

The title compound was prepared in a procedure analogous to that described for INTERMEDIATE 18. Mass spectrum (ESI) 277.0 (M+1).

INTERMEDIATE 29

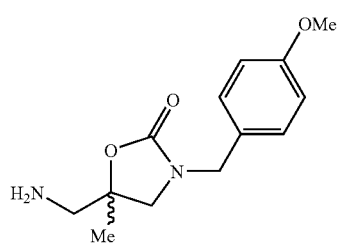

5-(Aminomethyl)-3-(4-methoxybenzyl)-5-methyl-1,3-oxazolidin-2-one

The title compound was prepared in a procedure analogous to that described for INTERMEDIATE 19. Mass spectrum (ESI) 251.0 (M+1).

Example 65

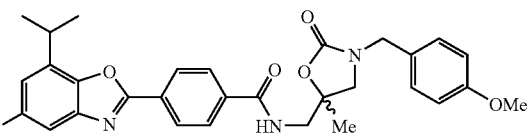

4-(5-Cyano-7-isopropyl-1,3-benzoxazol-2-yl)-N-{[3-(4-methoxybenzyl)-5-methyl-2-oxo-1,3-oxazolidin-5-yl]methyl}benzamide The title compound was prepared in a procedure analogous to that described for EXAMPLE 50. Mass spectrum (ESI) 539.1 (M+1). 1H NMR (500 MHz, CDCl3): δ 8.33 (d, J=7.7 Hz, 1H), 7.96 (s, 1H), 7.86 (d, J=8.0 Hz, 2H), 7.53 (s, 1H), 7.13 (d, J=8.0 Hz, 2H), 6.74 (d, J=8.2 Hz, 2H), 6.62 (bs, 1H), 4.36 (d, J=15.1 Hz, 1H), 4.28 (d, J=14.9 Hz, 1H), 3.85 (dd, J=14.9, 6.4 Hz, 1H), 3.71 (s, 3H), 3.55 (dd, J=14.8, 5.2 Hz, 1H), 3.50 (sept, J=6.6 Hz, 1H), 3.41 (d, J=9.2 Hz, 1H), 3.16 (d, J=8.9 Hz, 1H), 1.48 (s, 3H), 1.47 (d, J=6.4 Hz, 6H).

INTERMEDIATE 30

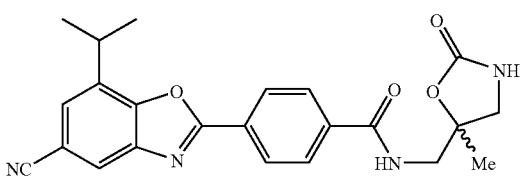

4-(5-Cyano-7-isopropyl-1,3-benzoxazol-2-yl)-N-[(5-methyl-2-oxo-1,3-oxazolidin-5-yl)methyl]benzamide To a solution of 4-(5-cyano-7-isopropyl-1,3-benzoxazol-2-yl)-N-{[3-(4-methoxybenzyl)-5-methyl-2-oxo-1,3-oxazolidin-5-yl]methyl}benzamide (598 mg, EXAMPLE 65) in 18.0 ml of acetonitrile and 6.0 ml of water was added 1.52 g of ceric ammonium nitrate. The mixture was stirred at room temperature for 15 h, and then concentrated in vacuo. The residue was dissolved in 10 ml of dichloromethane and purified via column chromatography on a Biotage Horizon 65i column eluting with 0% ethyl acetate in hexanes (1 column volume), followed by a gradient to 100% ethyl acetate in hexanes (over 10 column volumes), and held at 100% ethyl acetate for 2 column volumes to remove all the impurities. The column was then flushed with methanol (5 column vol-

Example 66

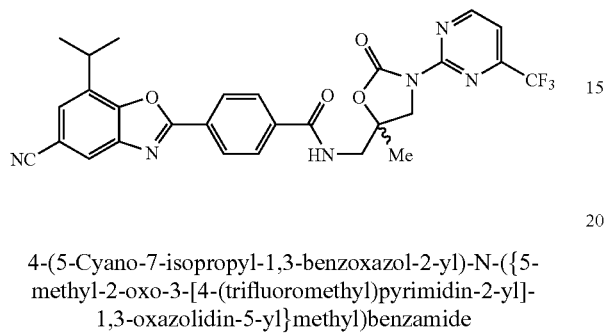

4-(5-Cyano-7-isopropyl-1,3-benzoxazol-2-yl)-N-({5-methyl-2-oxo-3-[4-(trifluoromethyl)pyrimidin-2-yl]-1,3-oxazolidin-5-yl}methyl)benzamide To a mixture was sodium hydride (9 mg, 60% dispersion) in 5 ml of dimethylformamide was added 4-(5-cyano-7-isopropyl-1,3-benzoxazol-2-yl)-N-[(5-methyl-2-oxo-1,3-oxazolidin-5-yl)methyl]benzamide (31 mg, EXAMPLE 65) followed by 2-chloro-4-trifluoromethylpyrimidine (14 mg). The mixture was stirred at 70° C. for 1 h. Excess sodium hydride was quenched by addition of 1 ml of methanol. The sample was then purified via mass-directed HPLC on a Kromasil C18 column eluting with a gradient of 10% acetonitrile in water (0.01% TFA) to 60% acetonitrile in water (0.01% TFA) providing the title compound (25 mg, 59%). Mass spectrum (ESI) 565.1 (M+1). 1H NMR (500 MHz, CDCl3): δ 8.94 (d, J=3.9 Hz, 1H), 8.33 (d, J=7.8 Hz, 2H), 7.95 (s, 1H), 7.94 (d, J=7.3 Hz, 2H), 7.52 (s, 1H), 7.36 (d, J=4.1 Hz, 1H), 6.69 (bs, 1H), 4.26 (d, J=11.2 Hz, 1H), 4.12 (d, J=10.7 Hz, 1H), 3.99 (dd, J=14.6, 6.2 Hz, 1H), 3.55 (dd, J=14.8, 6.1 Hz, 1H), 3.48 (sept, J=6.5 Hz, 1H), 1.66 (s, 3H), 1.46 (d, J=6.7 Hz, 6H).

INTERMEDIATE 31

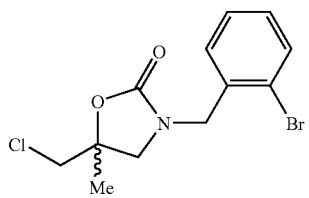

3-(2-Bromobenzyl)-5-(chloromethyl)-5-methyl-1,3-oxazolidin-2-one

The title compound was prepared in a procedure analogous to that described for INTERMEDIATE 27. Mass spectrum (ESI) 319.9 (M+1).

INTERMEDIATE 32

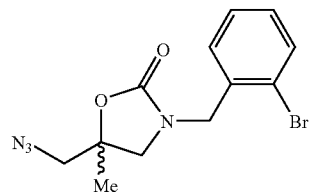

5-(Azidomethyl)-3-(2-bromobenzyl)-5-methyl-1,3-oxazolidin-2-one

The title compound was prepared in a procedure analogous to that described for INTERMEDIATE 18. Mass spectrum (ESI) 327.0 (M+1).

INTERMEDIATE 33

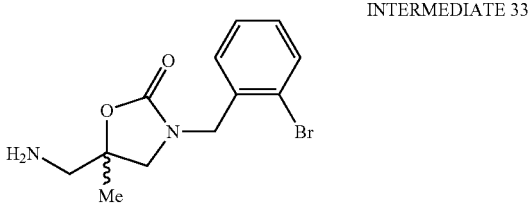

5-(Aminomethyl)-3-(2-bromobenzyl)-5-methyl-1,3-oxazolidin-2-one

The title compound was prepared in a procedure analogous to that described for INTERMEDIATE 19. Mass spectrum (ESI) 300.9 (M+1).

INTERMEDIATE 34

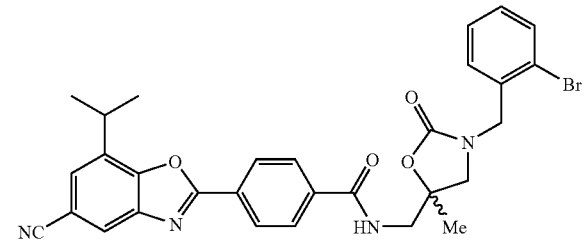

N-{[3-(2-Bromobenzyl)-5-methyl-2-oxo-1,3-oxazolidin-5-yl]methyl}-4-(5-cyano-7-isopropyl-1,3-benzoxazol-2-yl)benzamide The title compound was prepared in a procedure analogous to that described for EXAMPLE 50. Mass spectrum (ESI) 589.0 (M+1).

Example 67

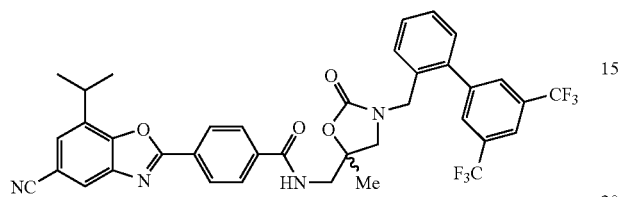

N-[(3-{[3',5'-Bis(trifluoromethyl)biphenyl-2-yl]methyl}-5-methyl-2-oxo-1,3-oxazolidin-5-yl)methyl]-4-(5-cyano-7-isopropyl-1,3-benzoxazol-2-yl)benzamide The title compound was prepared in a procedure analogous to that described for EXAMPLE 51. Mass spectrum (ESI) 721.3 (M+1). 1H NMR (500 MHz, CDCl3): δ 8.32 (d, J=8.4 Hz, 2H), 7.93 (s, 1H), 7.92 (d, J=8.4 Hz, 2H), 7.70 (s, 2H), 7.51 (s, 1H), 7.29 (m, 2H), 7.19 (m, 2H), 6.90 (t, J=6.1 Hz, 1H), 4.33 (d, J=3.0 Hz, 2H), 3.82 (dd, J=14.4, 6.8 Hz, 1H), 3.53 (dd, J=14.5, 5.8 Hz, 1H), 3.47 (sept, J=6.9 Hz, 1H), 3.33 (d, J=9.1 Hz, 2H), 3.00 (d, J=8.9 Hz, 1H), 1.45 (d, J=7.0 Hz, 6H), 1.43 (s, 3H).

Following the procedure described in EXAMPLE 67, the compounds listed in Table 6 were prepared:

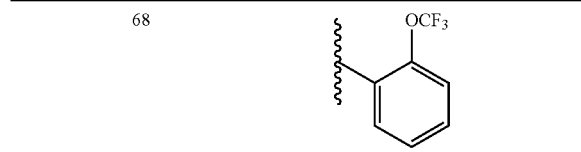

| EXAMPLE | R |
|---|---|
| 68 | 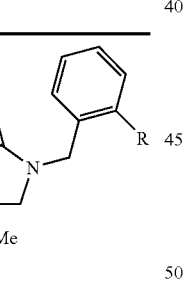 |
| 69 | 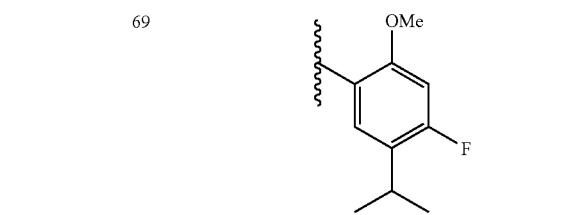 |
| 70 | 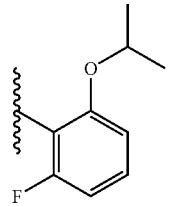 |
| 71 | 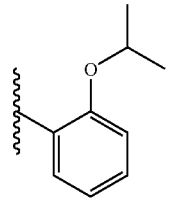 |
| 72 | 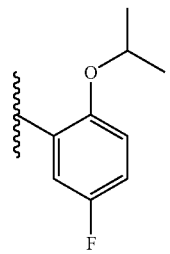 |
| 73 | 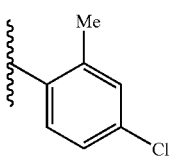 |
| 74 | 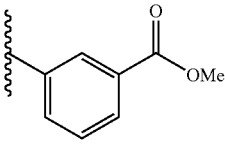 |
| 75 | 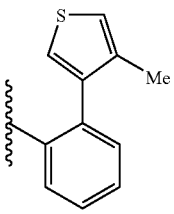 |

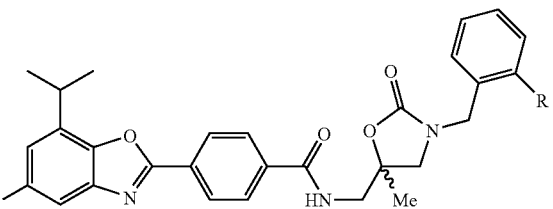

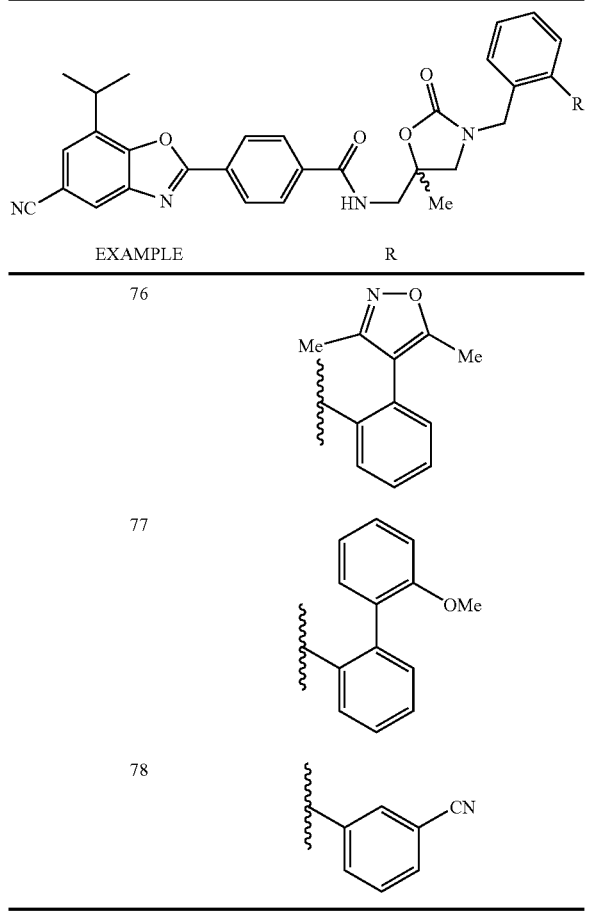

| EXAMPLE | R |
|---|---|
| 76 | (3,5-dimethylisoxazol-4-yl)phenyl group |
| 77 | (2-methoxybiphenyl) group |
| 78 | (3-cyanophenyl) group |

INTERMEDIATE 35

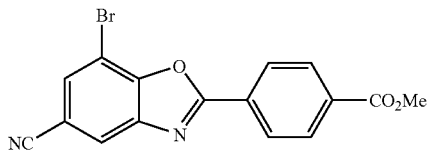

Methyl 4-(7-bromo-5-cyano-1,3-benzoxazol-2-yl)benzoate

Step A. 3-Bromo-4-hydroxy-5-nitrobenzonitrile

To a 5-l, 3-neck round-bottom flask fitted with a thermocouple, stirring paddle, and nitrogen line were added 3,5-dibromo-4-hydroxybenzonitrile (95 g) and glacial acetic acid (3.3 l). Sodium nitrite (120 g) was then added in small portions. The mixture was heated to 50° C. and stirred overnight at this temperature. The mixture was then allowed to cool and poured into a large extractor containing water (10 l). ethyl acetate (10 l) was added and the layers were separated. The aqueous layer was extracted with ethyl acetate (4 l) and the combined organic layers were washed with water and brine, and then dried over magnesium sulfate and concentrated in vacuo to provide 96.9 g of the desired product. Mass spectrum (ESI) 243.0 (M+).

Step B. 3-Amino-5-bromo-4-hydroxybenzonitrile

To a 22-l, 3-neck round-bottom flask fitted with a stirring paddle, a Claisen adapter fitted with a thermocouple and a condenser blanketed with nitrogen, and an addition funnel capped with a septum was added a mixture of 3-bromo-4-hydroxy-5-nitrobenzonitrile (96.9 g, Step A) in methanol (14 l). To this mixture was added iron (III) chloride (9.3 g) and activated charcoal (38 g, Darco 6-60, 100-mesh powder). The mixture was heated to reflux (65° C.) and stirred for 15 min at this temperature. Hydrazine (80 ml) was added to the refluxing mixture dropwise via addition funnel. Once the addition was complete, the mixture was stirred at reflux for 2 h. The mixture was then allowed to cool, filtered through Celite, washing with methanol, and concentrated to a red oil. A mixture of 300 ml of acetic acid and 700 ml of methanol was added and the mixture was concentrated again and then co-concentrated twice with 800 ml of toluene. The residue was purified by flash chromatography on an Isco Companion XL, 1.5 kg column, eluting with 3 column volumes of 30% ethyl acetate in hexanes, followed by a linear gradient of ethyl acetate in hexanes from 30 to 60% over 6 column volumes, followed by 2 column volumes of 60% ethyl acetate in hexanes to provide 40 g (55%) of the title compound. Mass spectrum (ESI) 214.9 (M+1).

Step C. Methyl 4-(7-bromo-5-cyano-1,3-benzoxazol-2-yl)benzoate

To a 3-l round-bottom flask fitted with a stir bar and a Claisen adapter fitted with a thermocouple and a condenser blanketed with nitrogen was added terephthalic acid monomethyl ester chloride (37.3 g) and a solution of 3-amino-5-bromo-4-hydroxybenzonitrile (40 g, Step B) in dioxane (675 ml). The mixture was heated to reflux and stirred at this temperature overnight. The mixture was then cooled to room temperature and the dioxane was removed in vacuo. The flask was fitted with a Dean-Stark trap and p-toluenesulfonic acid monohydrate (35.8 g) and toluene (2.5 l) were added. The mixture was heated to reflux and stirred at this temperature overnight. The mixture was then allowed to cool, transferred to a new 5-l flask, and concentrated to a brown solid. The crude product was triturated with methanol to provide 55.5 g (83%) of the title compound. 1H NMR (500 MHz, DMSO-d6): δ 8.50 (s, 1H), 8.34 (d, J=8.0 Hz, 2H), 8.29 (s, 1H), 8.19 (d, J=8.0 Hz, 2H), 3.91 (s, 3H).

INTERMEDIATE 36

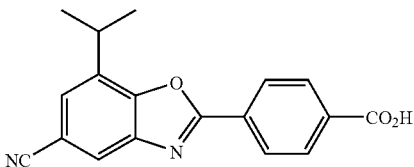

4-(5-Cyano-7-isopropyl-1,3-benzoxazol-2-yl)benzoic acid

Step A. Methyl 4-(5-cyano-7-isopropenyl-1,3-benzoxazol-2-yl)benzoate

To a 5-l, 3-neck round-bottom flask fitted with a stirring paddle, a condenser blanketed with nitrogen, and a thermocouple, was added 4-(7-bromo-5-cyano-1,3-benzoxazol-2- yl)benzoate (55.5 g, INTERMEDIATE 35), toluene (2 l), water (375 ml), ethanol (150 ml), 2M aqueous sodium carbonate (250 ml), and isoprenylboronic acid (83.4 g, INTERMEDIATE 37). The mixture was purged with nitrogen three times and then tetrakis(triphenylphosphine)palladium(0) (9.1 g) was added, and the mixture was purged three times with nitrogen. The mixture was heated to reflux (91° C.) and stirred at this temperature overnight. The mixture was then cooled to 20° C. and the product was filtered, washed with water, dried, and transferred to a 3-l round-bottom flask and rinsed with toluene (1 l). Residual solvent was removed in vacuo. Mass spectrum (ESI) 319.1 (M+1).

Step B. Methyl 4-(5-cyano-7-isopropyl-1,3-benzoxazol-2-yl)benzoate

To a 5-gallon reaction vessel was added methyl 4-(5-cyano-7-isopropenyl-1,3-benzoxazol-2-yl)benzoate (40.6 g, Step A), tetrahydrofuran (4 l), and 10% palladium on carbon (8 g). The reaction mixture was heated to 60° C. under 10 psi of hydrogen for 3 h, and then filtered through Celite, washing generously with dichloromethane. Concentration of the eluent in vacuo provided 40.5 g (99%) of the title compound. Mass spectrum (ESI) 321.1 (M+).

Step C. 4-(5-Cyano-7-isopropyl-1,3-benzoxazol-2-yl)benzoic acid

To a 5-l, round-bottom flask fitted with a stir bar and a Claisen adapter fitted with a thermocouple and a nitrogen line was added was added methyl 4-(5-cyano-7-isopropyl-1,3-benzoxazol-2-yl)benzoate (40.5 g, Step B) tetrahydrofuran (1.25 l), methanol (630 ml), water (315 ml), and lithium hydroxide monohydrate (10.7 g). The mixture was heated to 50° C. and stirred at this temperature for 1 h. The mixture was then cooled and concentrated to a thick slurry. 1N HCl (3.2 l) was added and an off-white solid formed. The mixture was stirred for 5 min and then filtered, washing with water (2×500 ml). The solid was transferred to a 2-l round-bottom flask, concentrated from toluene (1 l) and then dried in vacuo. Mass spectrum (ESI) 307.0 (M+1). 1H NMR (500 MHz, DMSO-d6): δ 8.69 (d, J=7.5 Hz, 2H), 8.28 (s, 1H), 8.16 (d, J=8.0 Hz, 2H), 7.81 (s, 1H), 3.46 (septet, J=6.5 Hz, 1H), 1.40 (d, H=7.0 Hz, 6H).

INTERMEDIATE 37

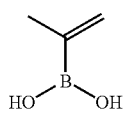

Isoprenylboronic Acid

To a 12-l, 3-neck round-bottom flask fitted with a stirring paddle, an addition funnel capped with a septum, and a Claisen adapter fitted with a thermocouple and a nitrogen line was added trimethyl borate (405 ml) and tetrahydrofuran (2.4 l). To this solution was added isoprenylmagnesium bromide (2.4 l of a 0.5 M solution in tetrahydrofuran) via the addition funnel, keeping the temperature below 30° C. using an ice-water bath. Upon completion of the addition, the mixture was stirred for 3 h at room temperature. The reaction mixture was poured into a large extractor containing 1N HCl (4 l). Ether (4 l) was added, the layers were separated, and the aqueous layer was extracted with ether (2 l). The combined organic layers were dried over magnesium sulfate and concentrated in vacuo, keeping the temperature below 30° C., to provide 197.3 g of the title compound. 1H NMR (500 MHz, CDCl3): δ 6.13 (s, 1H); 5.84 (s, 1H); 5.63 (app. d, J=12.1 Hz, 2H); 4.38 (br. s, 1H); 1.87 (app. d, J=21.7 Hz, 6H).

INTERMEDIATE 38

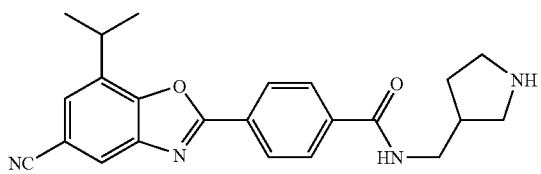

4-(5-Cyano-7-isopropyl-1,3-benzoxazol-2-yl)-N-(pyrrolidin-3-ylmethyl)benzamide

Step A. tert-Butyl 3-({[4-(5-cyano-7-isopropyl-1,3-benzoxazol-2-yl)benzoyl]amino}methyl)pyrrolidine-1-carboxylate The title compound was prepared from 4-(5-cyano-7-isopropyl-1,3-benzoxazol-2-yl)benzoic acid (INTERMEDIATE 36) and tert-butyl 3-(aminomethyl)pyrrolidine-1-carboxylate by a procedure analogous to that described in EXAMPLE 1. Mass spectrum (ESI) 489.3 (M+1).

Step B. 4-(5-Cyano-7-isopropyl-1,3-benzoxazol-2-yl)-N-(pyrrolidin-3-ylmethyl)benzamide To a solution of tert-butyl 3-({[4-(5-cyano-7-isopropyl-1,3-benzoxazol-2-yl)benzoyl]amino}methyl)pyrrolidine-1-carboxylate (910 mg) in dichloromethane (75 ml) was added 20 ml of trifluoroacetic acid. The mixture was stirred at room temperature for 2 h, and then concentrated in vacuo. The residue was basified by the addition of 75 ml of saturated aqueous sodium bicarbonate and diluted with 75 ml of ethyl acetate. The solids were filtered from both layers and dried in vacuo to provide the title compound (655 mg, 90%). Mass spectrum (ESI) 389.9 (M+1).

Example 79

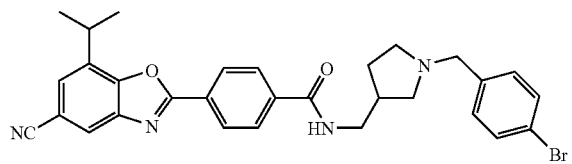

N-{[1-(4-Bromobenzyl)pyrrolidin-3-yl]methyl}-4-(5-cyano-7-isopropyl-1,3-benzoxazol-2-yl)benzamide To a solution of 4-(5-cyano-7-isopropyl-1,3-benzoxazol-2-yl)-N-(pyrrolidin-3-ylmethyl)benzamide (78 mg) in 2 ml of methanol was added 558 μl of triethylamine and 50 mg of 1-bromo-4-(bromomethyl)benzene. The solution was heated to 150° C. via microwave for 30 min, cooled, and purified via column chromatography on a Biotage Horizon 40M column eluting with 1 column volume of 100% hexanes, followed by a gradient of 0 to 100% ethyl acetate in hexanes over 10 column volumes, followed by 6 column volumes at 100% ethyl acetate to provide the title compound (75 mg, 68%). Mass spectrum (ESI) 559.0 (M+2). 1H NMR (500 MHz, CDCl3): δ 8.32 (d, J=8.5 Hz, 2H), 7.96 (s, 1H), 7.91 (d, J=8.2 Hz, 2H), 7.52 (s, 1H), 7.42 (d, J=8.2 Hz, 2H), 7.16 (d, J=8.2 Hz, 2H), 3.52 (m, 3H), 2.98 (td, J=9.1, 2.9, 1H), 2.76 (d, J=9.6 Hz, 1H), 2.58 (m, 2H), 2.32 (m, 1H), 2.14 (m, 1H), 1.68 (m, 1H), 1.48 (d, J=6.8 Hz, 6H).

Following the procedure described in EXAMPLE 79, the compounds listed in Table 9 were prepared:

TABLE 9

| EXAMPLE | R | MS (M + 1) |
|---|---|---|
| 80 | 4-biphenylmethyl | 555.7 |
| 81 | (2-cyanobiphenyl-4-yl)methyl | 580.6 |
| 82 | (9,10-dioxo-9,10-dihydroanthracen-2-yl)methyl | 609.3 |
| 83 | (5,5,8,8-tetramethyl-5,6,7,8-tetrahydronaphthalen-2-yl)methyl | 589.7 |

INTERMEDIATE 39

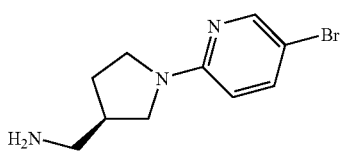

1-[(3R)-1-(5-Bromopyridin-2-yl)pyrrolidin-3-yl]methanamine

To a mixture of potassium carbonate (830 mg) in 20 ml of isopropanol was added tert-butyl [(3R)-pyrrolidin-3-ylmethyl]carbamate (601 mg) followed by 2,4-dibromopyrimidine (1.42 g). This mixture was heated to reflux for 8 h, at which point LC/MS analysis showed complete conversion to the desired product. The solvent was then removed in vacuo and the residue was taken up in ethyl acetate and filtered through a small plug of silica gel. The eluent was concentrated in vacuo and then dissolved in 50 ml of dichloromethane, to which was added 25 ml of trifluoroacetic acid. This mixture was heated to 40° C. for 30 min. The solution then was concentrated in vacuo and the residue was made basic by addition of 60 ml of a saturated solution of sodium bicarbonate. To this was added 60 ml of ethyl acetate and the phases were separated. The aqueous phase was extracted with another 60 ml of ethyl acetate and the combined organics were dried over sodium sulfate, filtered, and concentrated in vacuo to provide the title compound. Mass spectrum (ESI) 256.9 (M+2).

INTERMEDIATE 40

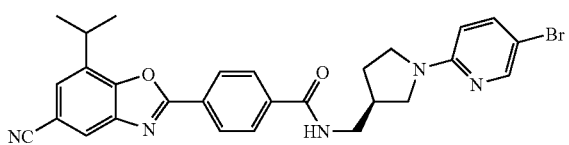

1-[(3S)-1-(5-romopyridin-2-yl)pyrrolidin-3-yl]methanamine

Starting from tert-butyl [(3S)-pyrrolidin-3-ylmethyl]carbamate, the title compound was prepared following a procedure analogous to that described for INTERMEDIATE 39. Mass spectrum (ESI) 256.9 (M+2).

Example 84

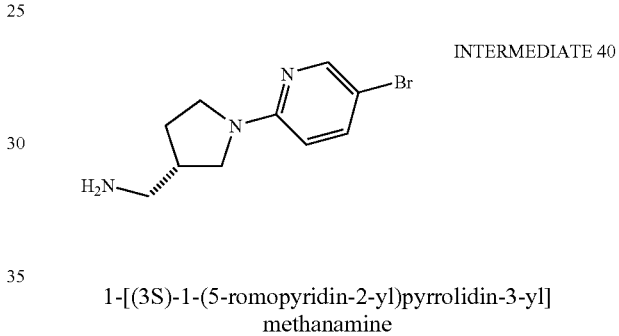

N-{[(3R)-1-(5-Bromopyridin-2-yl)pyrrolidin-3-yl]methyl}-4-(5-cyano-7-isopropyl-1,3-benzoxazol-2-yl)benzamide The title compound was prepared in a procedure analogous to that described for EXAMPLE 1. Mass spectrum (ESI) 546.0 (M+2). 1H NMR (500 MHz, CDCl3): δ 8.33 (d, J=8.4 Hz, 2H), 8.16 (d, J=2.3 Hz, 1H), 7.94 (d, J=8.3 Hz, 2H), 7.94 (s, 1H), 7.52 (s, 1H), 7.50 (dd, J=8.9 Hz, 2.5 Hz, 1H), 6.41 (t, J=5.8 Hz, 1H), 6.28 (d, J=8.9 Hz, 1H), 3.69 (m, 2H), 3.55 (m, 4H), 3.30 (dd, J=10.2 Hz, 6.7 Hz, 1H), 2.74 (sept, J=7.1 Hz, 1H), 2.25 (m, 1H), 1.89, (m, 1H), 1.46 (d, J=6.9 Hz, 6H).

Example 85

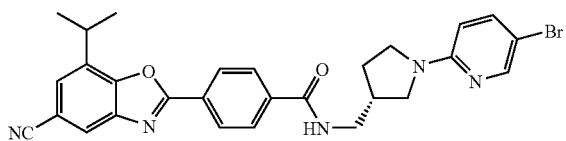

N-{[(3S)-1-(5-Bromopyridin-2-yl)pyrrolidin-3-yl]methyl}-4-(5-cyano-7-isopropyl-1,3-benzoxazol-2-yl)benzamide The title compound was prepared in a procedure analogous to that described for EXAMPLE 1. Mass spectrum (ESI) 546.0 (M+2). 1H NMR (500 MHz, CDCl3): δ 8.33 (d, J=8.4 Hz, 2H), 8.16 (d, J=2.3 Hz, 1H), 7.94 (d, J=8.3 Hz, 2H), 7.94 (s, 1H), 7.52 (s, 1H), 7.50 (dd, J=8.9 Hz, 2.5 Hz, 1H), 6.41 (t, J=5.8 Hz, 1H), 6.28 (d, J=8.9 Hz, 1H), 3.69 (m, 2H), 3.55 (m, 4H), 3.30 (dd, J=10.2 Hz, 6.7 Hz, 1H), 2.74 (sept, J=7.1 Hz, 1H), 2.25 (m, 1H), 1.89, (m, 1H), 1.46 (d, J=6.9 Hz, 6H).

Example 86

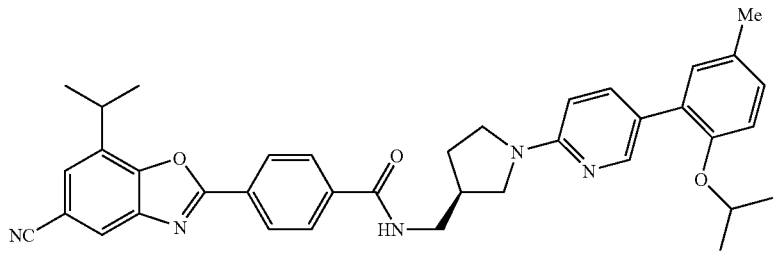

4-(5-Cyano-7-isopropyl-1,3-benzoxazol-2-yl)-N-({(3R)-1-[5-(2-isopropoxy-5-methylphenyl)pyridin-2-yl]pyrrolidin-3-yl}methyl)benzamide Sodium carbonate (100 µl, 2M aqueous), (2-isopropoxy-5-methylphenyl)boronic acid (39 mg), and N-{[(3R)-1-(5-bromopyridin-2-yl)pyrrolidin-3-yl]methyl}-4-(5-cyano-7-isopropyl-1,3-benzoxazol-2-yl)benzamide (EXAMPLE 84, 27 mg) were dissolved in toluene (2.1 ml), water (0.6 ml) and ethanol (0.3 ml). To this solution was added tetrakis(triphenylphosphine)palladium(0) (9 mg). The mixture was heated to 150° C. for 25 min via microwave, and then cooled and concentrated. The residue was dissolved in dichloromethane and purified via flash chromatography on a Biotage Horizon, 40 M column, eluting with 1 column volume of 100% ethyl acetate in hexanes, followed by a gradient of 0 to 100% ethyl acetate in hexanes over 10 column volumes, followed by 4 column volumes of 100% ethyl acetate to provide the title compound (26 mg, 84%). Mass spectrum (ESI) 614.6 (M+2). 1H NMR (500 MHz, CDCl3): δ 8.37 (d, J=2.3 Hz, 1H), 8.34 (d, J=8.2 Hz, 2H), 7.95 (d, J=8.2 Hz, 2H), 7.94 (s, 1H), 7.72 (dd, J=8.6 Hz, 2.3 Hz, 1H), 7.52 (s, 1H), 7.09 (s, 1H), 7.04 (dd, J=8.4 Hz, 2.1 Hz, 1H), 6.87 (d, J=8.2 Hz, 1H), 6.43 (d, J=8.7 Hz, 2H), 4.40 (sept, J=6.1 Hz, 1H), 3.79 (m, 2H), 3.73 (m, 1H), 3.51 (m, 3H), 3.41 (m, 1H), 2.76 (sept, J=6.9 Hz, 1H), 2.32 (s, 3H), 2.27 (m, 1H), 1.91, (m, 1H), 1.46 (d, J=6.8 Hz, 6H), 1.24 (d, J=5.9 Hz, 6H).

Example 87

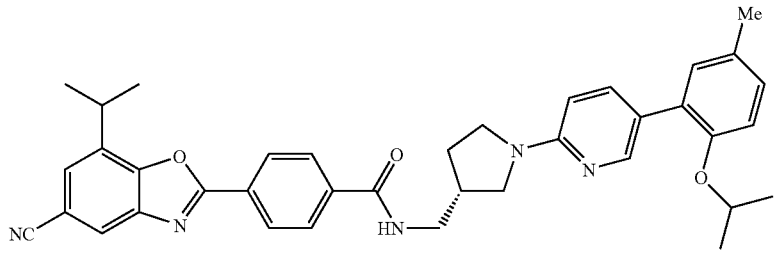

4-(5-Cyano-7-isopropyl-1,3-benzoxazol-2-yl)-N-({(3S)-1-[5-(2-isopropoxy-5-methylphenyl)pyridin-2-yl]pyrrolidin-3-yl}methyl)benzamide Sodium carbonate (100 µl, 2M aqueous), (2-isopropoxy-5-methylphenyl)boronic acid (39 mg), and N-{[(3R)-1-(5-bromopyridin-2-yl)pyrrolidin-3-yl]methyl}-4-(5-cyano-7-isopropyl-1,3-benzoxazol-2-yl)benzamide (EXAMPLE 85, 27 mg) were dissolved in toluene (2.1 ml), water (0.6 ml) and ethanol (0.3 ml). To this solution was added tetrakis(triphenylphosphine)palladium(0) (9 mg). The mixture was heated to 150° C. for 25 min via microwave, and then cooled and concentrated. The residue was dissolved in dichloromethane, and purified via flash chromatography on a Biotage Horizon, 40 M column, eluting with 1 column volume of 100% hexanes, followed by a gradient of 0 to 100% ethyl acetate in hexanes over 10 column volumes, followed by 4 column volumes of 100% ethyl acetate to provide the title compound (23 mg, 74%). Mass spectrum (ESI) 614.6 (M+2). 1H NMR (500 MHz, CDCl3): δ 8.37 (d, J=2.3 Hz, 1H), 8.34 (d, J=8.2 Hz, 2H), 7.95 (d, J=8.2 Hz, 2H), 7.94 (s, 1H), 7.72 (dd, J=8.6 Hz, 2.3 Hz, 1H), 7.52 (s, 1H), 7.09 (s, 1H), 7.04 (dd, J=8.4 Hz, 2.1 Hz, 1H), 6.87 (d, J=8.2 Hz, 1H), 6.43 (d, J=8.7 Hz, 2H), 4.40 (sept, J=6.1 Hz, 1H), 3.79 (m, 2H), 3.73 (m, 1H), 3.51 (m, 3H), 3.41 (m, 1H), 2.76 (sept, J=6.9 Hz, 1H), 2.32 (s, 3H), 2.27 (m, 1H), 1.91, (m, 1H), 1.46 (d, J=6.8 Hz, 6H), 1.24 (d, J=5.9 Hz, 6H).

Example 88

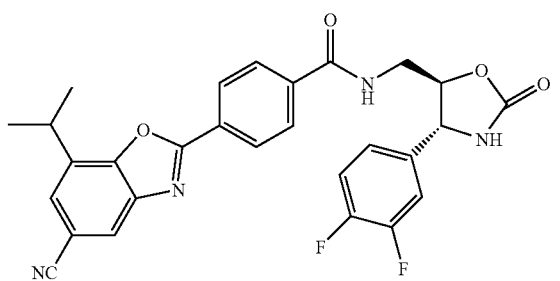

4-(5-Cyano-7-isopropyl-1,3-benzoxazol-2-yl)-N-{[(4R,5R)-4-(3,4-difluorophenyl)-2-oxo-1,3-oxazolidin-5-yl]methyl}benzamide A suspension of 4-(5-cyano-7-isopropyl-1,3-benzoxazol-2-yl)benzoic acid (INTERMEDIATE 2, 67 mg, 0.219 mmol), o-benzotriazol-1-yl-tetramethyluronium hexafluorophosphate (166 mg, 0.438 mmol), 1-hydroxybenzotriazole hydrate (50 mg, 0.327 mmol), and diisopropylethylamine (0.2 ml, 1.145 mmol) in dichloromethane (1 ml) was stirred for 5 min at room temperature, and then a solution of (4R, 5R)-5-(aminomethyl)-4-(3,4-difluorophenyl)-1,3-oxazolidin-2-one in dichloromethane (1 ml) was added. The mixture was stirred overnight at 25° C. The mixture was diluted with 10 ml of saturated sodium bicarbonate solution and 10 ml of dichloromethane. The phases were separated and the aqueous phase was extracted with 2×10 ml of dichloromethane. The combined organics were washed with 10 ml of brine, dried (sodium sulfate), and concentrated. The residue was purified by flash chromatography on a Biotage Horizon, 25M column, eluting with 1 column volume of 100% dichloromethane followed by a gradient of 0 to 100% ethyl acetate in dichloromethane over 10 column volumes, to provide the title compound (51 mg, 0.099 mmol, 45.1% yield). Mass spectrum (ESI) 517.2 (M+2). 1H NMR (500 MHz, CDCl3): δ 8.36 (d, J=8.5 Hz, 2H), 8.05 (d, J=8.5 Hz, 2H), 7.95 (s, 1H), 7.52 (s, 1H), 7.35 (m, 1H), 7.23 (m, 2H), 6.02 (s, 1H), 4.79 (d, J=7.5 Hz, 1H), 4.48 (m, 1H), 3.05 (m, 1H), 3.83 (m, 1H), 3.49 (m, 2H), 1.47 (d, J=7.0 Hz, 6H).

Examples 89 and 90

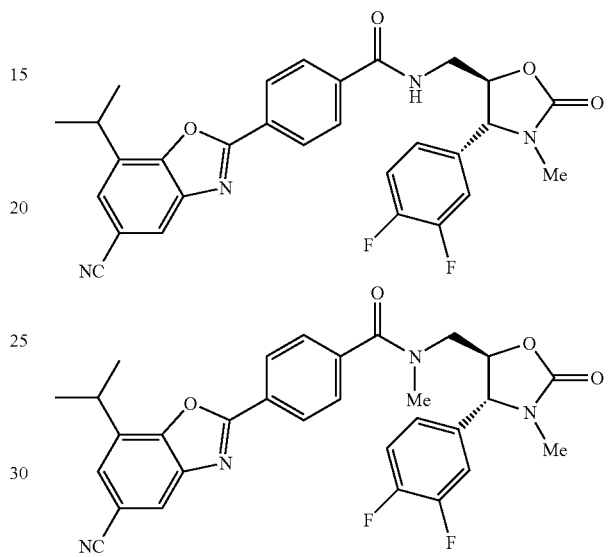

4-(5-Cyano-7-isopropyl-1,3-benzoxazol-2-yl)-N-{[(4R,5R)-4-(3,4-difluorophenyl)-3-methyl-2-oxo-1,3-oxazolidin-5-yl]methyl}benzamide and 4-(5-cyano-7-isopropyl-1,3-benzoxazol-2-yl)-N-{[(4R,5R)-4-(3,4-difluorophenyl)-3-methyl-2-oxo-1,3-oxazolidin-5-yl]methyl}-N-methylbenzamide To a 0° C. solution of 4-(5-cyano-7-isopropyl-1,3-benzoxazol-2-yl)-N-{[(4R,5R)-4-(3,4-difluorophenyl)-2-oxo-1,3-oxazolidin-5-yl]methyl}benzamide (EXAMPLE 88, 30 mg, 0.058 mmol) in tetrahydrofuran (1 ml) was added sodium hydride (4 mg, 0.100 mmol). The mixture was stirred at 0° C. for 5 min, and then iodomethane (10 µl, 0.160 mmol) was added and the mixture was stirred overnight. The mixture was then purified by flash chromatography on a Biotage Horizon, 25S column, eluting with 1 column volume of 100% dichloromethane followed by a gradient of 0 to 50% methanol in dichloromethane over 10 column volumes, to provide a mixture of the title compounds. This mixture was further purified by preparative thin-layer chromatography on a 1000-µm plate, eluting with 95:5 dichloromethane-methanol to provide the monomethylated (2.5 mg, 4.71 µmol, 8.11% yield) and dimethylated title compounds (7.5 mg, 0.014 mmol, 23.71% yield).

Data for 4-(5-cyano-7-isopropyl-1,3-benzoxazol-2-yl)-N-{[(4R,5R)-4-(3,4-difluorophenyl)-3-methyl-2-oxo-1,3-oxazolidin-5-yl]methyl}benzamide: Mass spectrum (ESI) 531.1 (M+1). 1H NMR (500 MHz, CDCl3): δ 8.36 (d, J=8.5 Hz, 2H), 7.98 (d, J=8.5 Hz, 2H), 7.95 (s, 1H), 7.53 (s, 1H), 7.25 (m, 2H), 7.18 (m, 1H), 6.80 (br t, J=6.5 Hz, 1H), 4.46 (d, J=7.5 Hz, 1H), 4.40 (m, 1H), 3.98 (m, 1H), 3.82 (m, 1H), 3.49 (septet, J=7.0 Hz, 1H), 2.72 (s, 3H), 1.47 (d, J=7.0 Hz, 6H).

Data for 4-(5-cyano-7-isopropyl-1,3-benzoxazol-2-yl)-N-{[(4R,5R)-4-(3,4-difluorophenyl)-3-methyl-2-oxo-1,3-oxazolidin-5-yl]methyl}-N-methylbenzamide: Mass spectrum (ESI) 545.1 (M+1). 1H NMR (500 MHz, CDCl3): δ 8.33 (d, J=8.0 Hz, 2H), 7.94 (s, 1H), 7.57 (d, J=8.0 Hz, 2H), 7.52 (s, 1H), 7.25 (m, 2H), 7.18 (m, 1H), 4.55 (br s, 2H), 3.95 (m, 2H), 3.47 (septet, J=7.0 Hz, 1H), 3.16 (s, 3H), 2.76 (s, 3H), 1.46 (d, J=7.0 Hz, 6H).

What is claimed is:

1. A compound having Formula I, or a pharmaceutically acceptable salt thereof, wherein

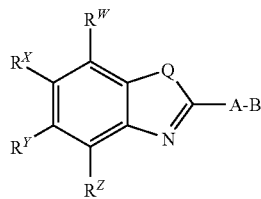

I

Q is selected from the group consisting of O, S, and —N($R^2$)—;

A is 1,4-phenylene, wherein A is optionally substituted with 1-3 substituent groups $R^1$;

Each $R^1$ is independently selected from the group consisting of halogen, $C_1$-$C_3$alkyl, $C_2$-$C_3$alkenyl, $C_2$-$C_3$alkynyl, and —O$C_1$-$C_3$alkyl, wherein each alkyl, alkenyl, and alkynyl substituent is optionally substituted with 1-5 halogens;

Each $R^2$ is independently selected from the group consisting of H, $C_1$-$C_3$alkyl, $C_2$-$C_3$alkenyl, and $C_2$-$C_3$alkynyl, wherein each alkyl, alkenyl, and alkynyl substituent is optionally substituted with 1-5 halogens;

$R^W$ is selected from the group consisting of (a) $C_1$-$C_5$alkyl which is optionally substituted with 1-5 halogens, (b) $C_{2-5}$ alkenyl which is optionally substituted with 1-5 halogens; (c) —O$C_1$-$C_5$ alkyl which is optionally substituted with 1-5 halogens, (d) —S$C_1$-$C_5$ alkyl which is optionally substituted with 1-5 halogens, (e) —O$C_{2-5}$ alkenyl which is optionally substituted with 1-5 halogens, (f) $C_3$-$C_6$cycloalkyl, (g) phenyl, (h) a 5-6 membered saturated or partly unsaturated heterocyclic group having 1-3 heteroatoms independently selected from N, S and O, (i) a 5-7 membered heteroaromatic group having 1-3 heteroatoms independently selected from N, S, and O, (j) —C(=O)O$C_{1-3}$alkyl which is optionally substituted with 1-5 halogens, and (k) —C(=O)OH, wherein said $C_3$-$C_6$cycloalkyl, phenyl, 5-6 membered saturated or partly unsaturated heterocyclic group, and 5-7 membered heteroaromatic group are optionally substituted with 1-3 substituents independently selected from halogen, $CH_3$, $CF_3$, —O$CH_3$, and —O$CF_3$;

$R^Y$ is selected from the group consisting of halogen, $CH_3$, $CF_3$, —O$CH_3$, —O$CF_3$, —CN, phenyl, and a 6-membered heteroaromatic group having 1-2 N, wherein phenyl and the 6-membered heteroaromatic group are optionally substituted with 1-3 substituents independently selected from halogen, $CH_3$, $CF_3$, —O$CH_3$, and —O$CF_3$;

$R^X$ and $R^Z$ are each selected from the group consisting of H, halogen, $CH_3$, $CF_3$, —O$CH_3$, and —O$CF_3$;

B is —C(=O)N($R^3$)($CR^4R^5$)$_x$($CR^6R^7$)$_y$$D^2$;

$R^3$ is selected from the group consisting of H and $C_1$-$C_3$alkyl;

$R^4$ is selected from the group consisting of H, $C_1$-$C_3$alkyl, $CF_3$, —C(=O)OH, and —C(=O)O$C_1$-$C_3$alkyl;

$R^5$ is selected from the group consisting of H, $C_1$-$C_3$alkyl, and $CF_3$;

$R^6$ is selected from the group consisting of H, $C_1$-$C_3$alkyl, $CF_3$, —C(=O)OH, and —C(=O)O$C_1$-$C_3$alkyl;

$R^7$ is selected from the group consisting of H, $C_1$-$C_3$alkyl, $CF_3$, and phenyl, which is optionally substituted with 1-3 groups independently selected from halogen, $CH_3$, $CF_3$, —O$CH_3$, and —O$CF_3$;

x is 0 or 1;

y is 0, 1, or 2;

$D^2$ is a cyclic group selected from 5-membered saturated and partly unsaturated heterocyclic groups, wherein $D^2$ comprises one ring member —N($R^8$)—, optionally 1-2 ring members independently selected from —O— and —S—, optionally one carbonyl group, and optionally 1-2 double bonds, wherein $D^2$ is optionally fused to a phenyl ring or to a $C_5$-$C_7$Cycloalkyl, wherein $D^2$ is connected to the right hand side of the structure represented by Formula I through a carbon atom of $D^2$, wherein $D^2$ is optionally substituted with 1-3 substituents independently selected from halogen, —CN, —$NO_2$, —N($R^3$)$_2$—, $C_1$-$C_3$alkyl, $CF_3$, —O$CH_3$, phenyl, pyridyl, and —O$CF_3$, and optionally with 1 group $C_1$-$C_5$alkylene-phenyl, wherein phenyl and pyridyl in all uses are optionally substituted with 1-3 substituent groups independently selected from halogen, $CH_3$, $CF_3$, —O$CH_3$, and —O$CF_3$;

$R^8$ is selected from the group consisting of H, $C_1$-$C_9$alkyl, —C(=O)O$C_1$-$C_9$alkyl, —C(=O)$C_1$-$C_9$alkyl, —S(O)$_{1-2}$$C_1$-$C_9$alkyl, —C(=O)N($R^9$)$_2$, —$C_1$-$C_3$alkylene-C(=O)O$C_1$-$C_6$alkyl, —$C_1$-$C_5$alkylene-O$C_1$-$C_9$alkyl, and a cyclic group $D^4$ bonded to the N to which $R^8$ is connected or to a difunctional linking group $L^4$ which is bonded to the N to which $R^8$ is connected, wherein the $C_1$-$C_9$alkyl and $C_1$-$C_6$alkyl groups in all uses are optionally substituted with 1-9 halogens;

Wherein $D^4$ is selected from the group consisting of (a) phenyl, (b) naphthyl, (c) $C_3$-$C_8$cycloalkyl optionally having 1-2 double bonds, (d) a saturated or partially unsaturated monocyclic or bicyclic 4-10 membered heterocycle having 1-3 heteroatoms independently selected from N, O, and S and optionally one —C(=O)— group, said heterocycle optionally having 1-2 double bonds, (e) a monocyclic or bicyclic 5-12 membered heteroaromatic group having 1-3 heteroatoms independently selected from N, S, and O and optionally having one —C(=O)— group, (f) tetralin, and (g) anthraquinone;

$L^4$ is selected from the group consisting of —C(=O)—, —C(=O)O—, —S(O)$_2$—, —C(=O)N($R^3$)—, —S(O)$_2$ N($R^3$)—, —$C_1$-$C_7$alkylene-, —C(=O)$C_1$-$C_7$alkylene-, —$C_2$-$C_4$alkenylene-, —C(=O)$C_1$-$C_7$alkylene-N($R^3$)—, —C(=O)O$C_1$-$C_7$alkylene-, —S(O)$_2$$C_1$-$C_7$alkylene-, —C(=O)N($R^3$)$C_1$-$C_7$alkylene-, —S(O)$_2$N($R^3$)$C_1$-$C_7$alkylene-, —$C_1$-$C_7$alkylene-N($R^3$)S(O)$_2$—, —$C_1$-$C_7$alkylene-S(O)$_2$N($R^3$)—, —$C_1$-$C_7$alkylene-N($R^3$)C(=O)—, and —$C_1$-$C_7$alkylene-C(=O)N($R^3$)—, wherein —$C_1$-$C_7$alkylene- optionally comprises a double bond between two adjacent carbons and optionally comprises a difunctional group selected from O, S, —S(O)$_2$—, —$NR^3$—, —C(=O)—, —N($R^3$)C(=O)—, and —N($R^3$)S(O)$_2$— between two adjacent carbons, wherein $D^4$ is optionally substituted with 1-4 substituents independently selected from halogen, —CN, —$NO_2$, —OH, $C_1$-$C_7$alkyl, $C_2$-$C_7$alkenyl, $CF_3$, —O$C_1$-

C₅alkyl, —C₁-C₅alkylene-OC₁-C₅alkyl, —OCF₃, —NHC(=O)C₁-C₅alkyl, NHC(=O)CH₂CO₂C₁-C₃alkyl, —N(R³)₂—, —C(=O)OH, and —C(=O)OC₁-C₇alkyl, and is optionally substituted with one cyclic group D⁶ bonded directly to D⁴ or connected to D⁴ through a linking group L⁶, wherein D⁶ has the same selections as D⁴, and L⁶ has the same selections as L⁴, and D6 is optionally substituted with 1-3 substituents independently selected from halogen, —CN, —NO₂, —OH, C₁-C₇alkyl, C₂-C₇alkenyl, CF₃, —OC₁-C₅alkyl, —C₁-C₅alkylene-OC₁-C₅alkyl, —OCF₃, —N(R³)₂—, —C(=O)OH, and —C(=O)OC₁-C₇alkyl, wherein the C₁-C₇alkyl, C₂-C₇alkenyl, and —OC₁-C₅alkyl groups in all uses in substituents on D4 and D6 are optionally substituted with 1-5 halogens; and Each R⁹ is independently selected from the group consisting of H, C₁-C₇alkyl, C₂-C₇alkenyl, and C₂-C₇alkynyl, wherein said C₁-C₇alkyl, C₂-C₇alkenyl, and C₂-C₇alkynyl are optionally substituted with 1-9 halogens.

2. The compound of claim 1 having Formula Ia, or a pharmaceutically acceptable salt thereof:

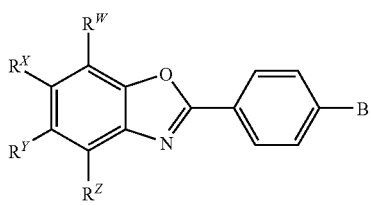

Ia wherein R^W is selected from the group consisting of (a) C₁-C₅alkyl which is optionally substituted with 1-5 F, (b) C₂₋₃ alkenyl which is optionally substituted with 1-3 F, (c) —OC₁-C₃ alkyl which is optionally substituted with 1-3 F, (d) —SC₁-C₃ alkyl which is optionally substituted with 1-3 F, (e) —OC₂₋₃ alkenyl which is optionally substituted with 1-3 F, (f) C₃-C₆cycloalkyl, (g) phenyl, (h) pyridyl, (i) —C(=O)OC₁₋₃alkyl which is optionally substituted with 1-3 F, and (k) —C(=O)OH, wherein said C₃-C₆cycloalkyl, phenyl, and pyridinyl substituents are optionally substituted with 1-3 substituents independently selected from halogen, CH₃, CF₃, —OCH₃, and —OCF₃;

R^Y is selected from the group consisting of halogen, CH₃, CF₃, —OCH₃, —OCF₃, and —CN; and R^X and R^Z are each selected the group consisting of H, halogen, CH₃, CF₃, —OCH₃, and —OCF₃.

3. The compound of claim 1 having Formula Ib, or a pharmaceutically acceptable salt thereof:

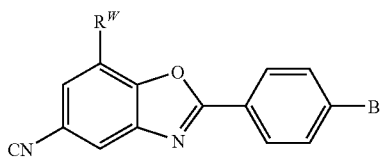

Ib wherein R^W is selected from the group consisting of C₁-C₄alkyl which is optionally substituted with 1-3 F, C₂₋₃ alkenyl, —OCH₃, —OCF₃, —SCH₃, —SCF₃, cyclopropyl, —C(=O)OC₁₋₃alkyl, and phenyl which is optionally substituted with 1-3 substituents independently selected from halogen, CH₃, CF₃, —OCH₃, and —OCF₃;

D² is a cyclic group selected from 1,3-oxazolidin-2-one and pyrrolidine;

R³ is selected from H and CH₃;

R⁴ and R⁵ are H;

x is 1; and y is 0.

4. The compound of claim 3, wherein

R^W is isopropyl;

D² is selected from 1,3-oxazolidin-2-one and pyrrolidine, and is optionally substituted with 1-2 CH₃ groups and optionally one phenyl group, wherein phenyl is optionally substituted with 1-3 groups independently selected from F, Cl, CH₃, CF₃, —OCH₃ and —OCF₃, and R⁸ is attached to the N of D²;

R⁸ is selected from the group consisting of H, C₁-C₃alkyl, pyridyl, pyrimidinyl, —CH₂-phenyl, —CH₂-anthraquinone, and —CH₂-tetralin, wherein the non-aromatic portion of the tetralin ring is optionally substituted with 1-4 CH₃ groups, wherein the pyridyl, pyrimidinyl, and phenyl rings of R⁸ are optionally substituted with 1-2 substituents independently selected from F, Cl, Br, C₁-C₄alkyl, CF₃, —OC₁-C₄alkyl, —OCF₃, C₂-C₅alkenyl, —NO₂, —NHC(=O)C₁-C₅alkyl, and —NHC(=O)CH₂CO₂C₁-C₃alkyl, and are optionally substituted with one cyclic group D⁶, which is connected directly to the aromatic ring of R⁸ or is connected to the aromatic ring of R⁸ through a linking group L⁶;

with the proviso that if R⁸ is H or C₁-C₃alkyl, then D² is substituted with one phenyl group which is optionally substituted with 1-3 groups independently selected from F, Cl, CH₃, CF₃, —OCH₃ and —OCF₃, and D² is optionally also substituted with one CH₃ group;

D⁶ is selected from the group consisting of phenyl, pyridyl, C₅-C₆cycloalkyl, C₅-C₆cycloalkenyl, thienyl, pyrazolyl, oxazolyl, and isoxazolyl, wherein D⁶ is optionally substituted with 1-3 substituent groups independently selected from halogen, C₁-C₅alkyl, —OC₁-C₅alkyl, CF₃, —OCF₃, —CO₂H, —C(=O)NH₂, —NHC(=O)C₁-C₅alkyl, —CO₂C₁-C₃alkyl, —CN, —OH, —NO₂, —CH₂OC₁-C₂alkyl, and optionally one cyclic group selected from 1,3-dioxolanyl, thienyl, pyrazolyl, isoxazolyl, and phenyl, wherein the cyclic group is optionally substituted with 1-2 groups independently selected from CH₃, —OCH₃, CF₃, —OCF₃, and halogen; and the optional linking group L⁶ is selected from the difunctional groups —C₂-C₄alkenylene- and —NHC(=O)—.

5. The compound of claim 4, having Formula Ic, or a pharmaceutically acceptable salt thereof:

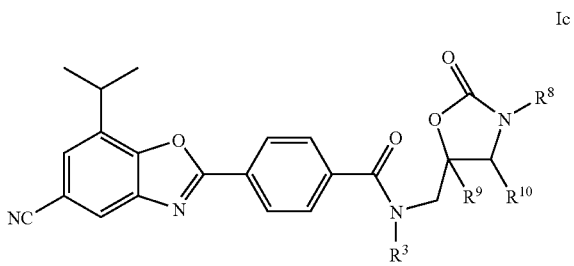

Ic wherein R³ and R⁹ are independently selected from H and CH₃;

R[8] is H or CH$_3$; and

R[10] is phenyl, which is optionally substituted with 1-2 groups independently selected from F, Cl, CH$_3$, CF$_3$, —OCH$_3$, and —OCF$_3$—.

6. The compound of claim 4, having Formula Ic, or a pharmaceutically acceptable salt thereof:

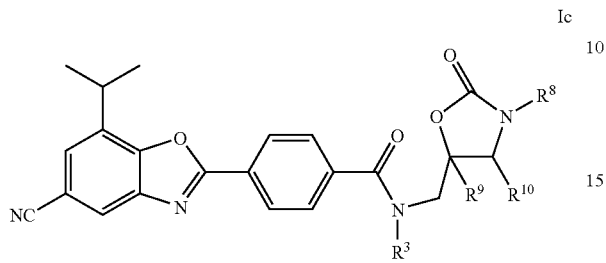

Ic wherein R[3] and R[9] are independently selected from H and CH$_3$;

R[10] is H;

R[8] is selected from the group consisting of pyridyl, pyrimidinyl, and —CH$_2$-phenyl, wherein the pyridyl, pyrimidinyl, and phenyl rings of R[8] are optionally substituted with 1-2 substituents independently selected from F, Cl, Br, C$_1$-C$_4$alkyl, CF$_3$, —OC$_1$-C$_4$alkyl, —OCF$_3$, C$_2$-C$_5$alkenyl, —NO$_2$, —NHC(=O)C$_1$-C$_5$alkyl, and —NHC(=O)CH$_2$CO$_2$C$_1$-C$_3$alkyl, and are optionally substituted with one cyclic group D[6], which is connected directly to the pyridyl, pyrimidinyl or phenyl ring of R[8] or is connected to the pyridyl, pyrimidinyl or phenyl ring of R[8] through a linking group L[6];

wherein D[6] is selected from the group consisting of phenyl, pyridyl, C$_5$-C$_6$cycloalkyl, C$_5$-C$_6$cycloalkenyl, thienyl, pyrazolyl, oxazolyl, and isoxazolyl, wherein D[6] is optionally substituted with 1-3 substituent groups independently selected from halogen, C$_1$-C$_5$alkyl, —OC$_1$-C$_5$alkyl, CF$_3$, —OCF$_3$, —CO$_2$H, —C(=O)NH$_2$, —NHC(=O)C$_1$-C$_5$alkyl, —CO$_2$C$_1$-C$_3$alkyl, —CN, —OH, —NO$_2$, —CH$_2$OC$_1$-C$_2$alkyl, and optionally one cyclic group selected from 1,3-dioxolanyl, thienyl, pyrazolyl, isoxazolyl, and phenyl, wherein the cyclic group is optionally substituted with 1-2 groups independently selected from CH$_3$, —OCH$_3$, CF$_3$, —OCF$_3$, and halogen; and wherein the optional linking group L[6] is selected from the difunctional groups —C$_2$-C$_4$alkenylene- and —NHC(=O)—.

7. The compound of claim 1, which is selected from the group consisting of the following compounds, or a pharmaceutically acceptable salt thereof:

| Ex. | Structure |
|---|---|
| 1 | 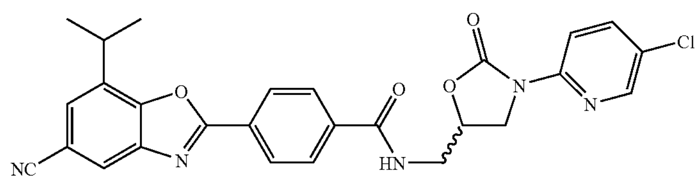 |
| 2 | 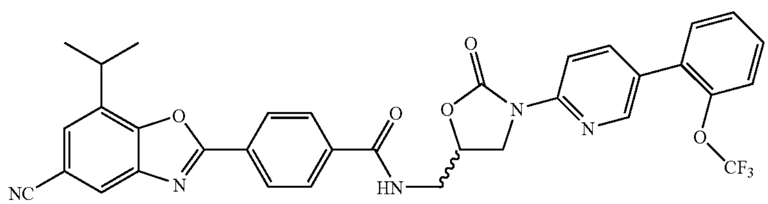 |
| 27 | 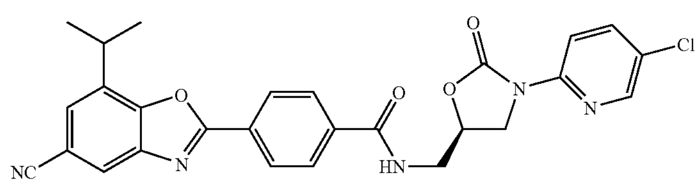 |
| 28 | 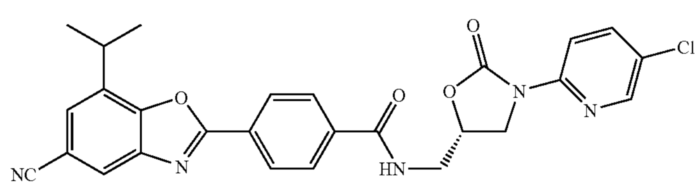 |

-continued
| Ex. | Structure |
|---|---|
| 29 | 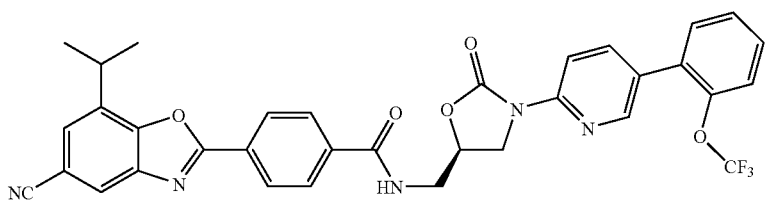 |
| 40 | 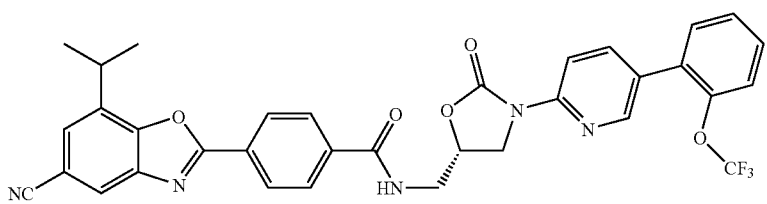 |
| 49 | 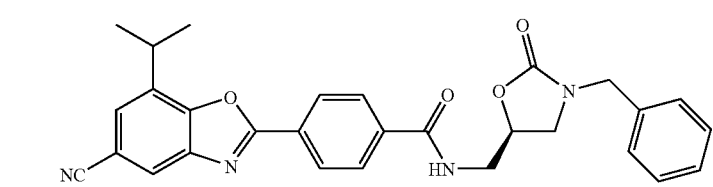 |
| 50 | 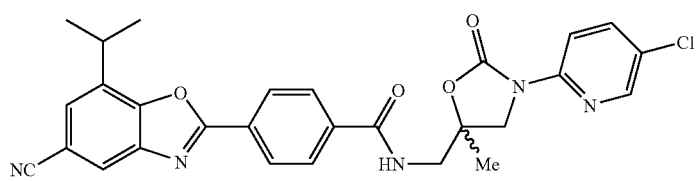 |
| 51 | 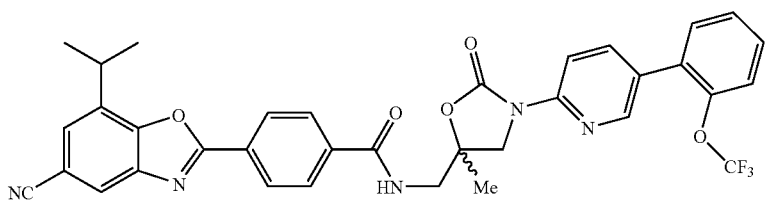 |
| 57 | 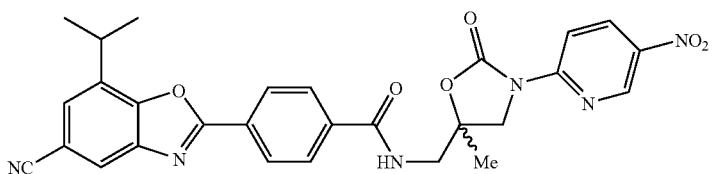 |
| 58 | 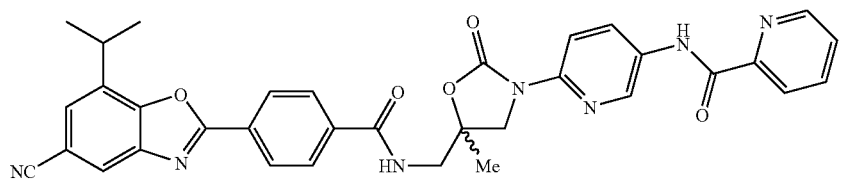 |
| 64 | 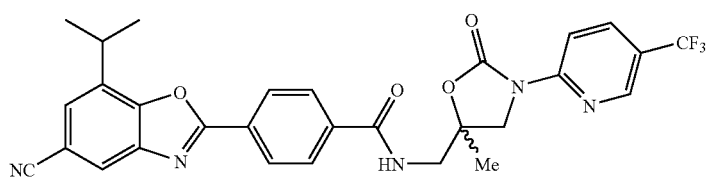 |

| Ex. | Structure |
|---|---|
| 65 | 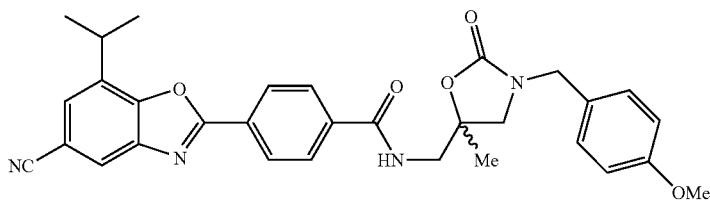 |
| 66 | 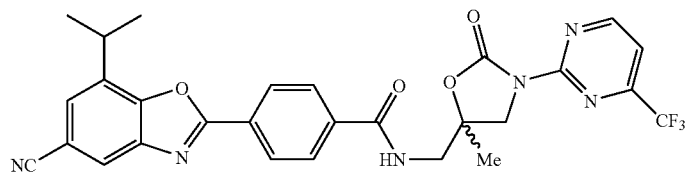 |
| 67 | 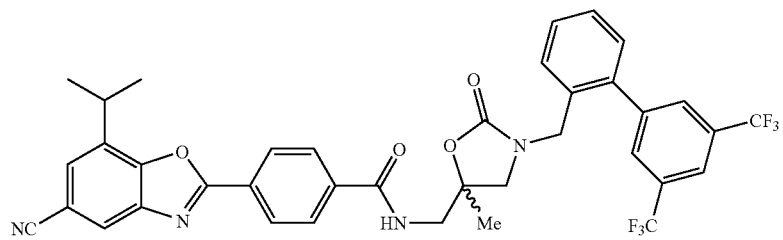 |
| 79 | 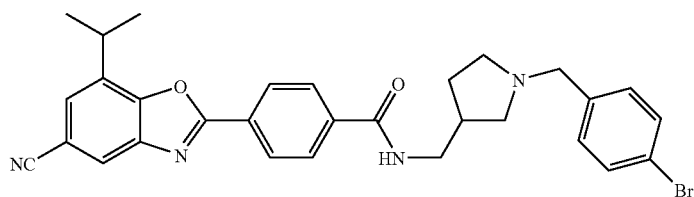 |
| 84 | 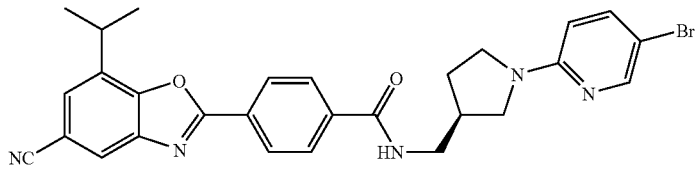 |
| 85 | 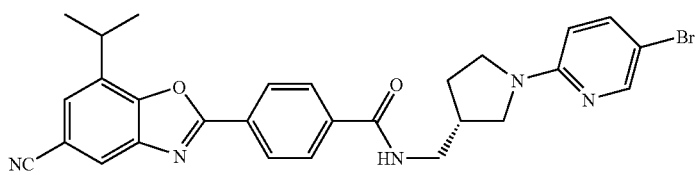 |

| Ex. | Structure |
|---|---|
| 86 | 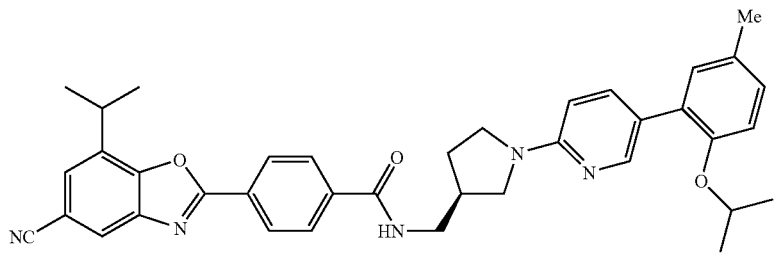 |
| 87 | 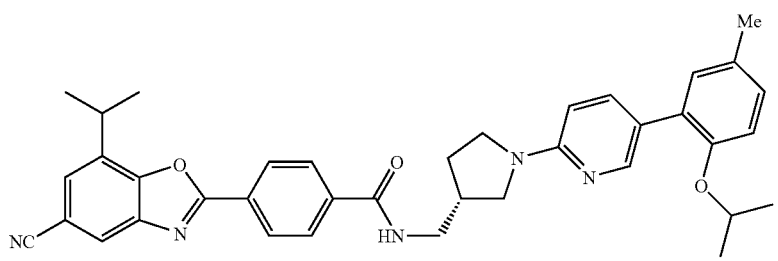 |
| 88 | 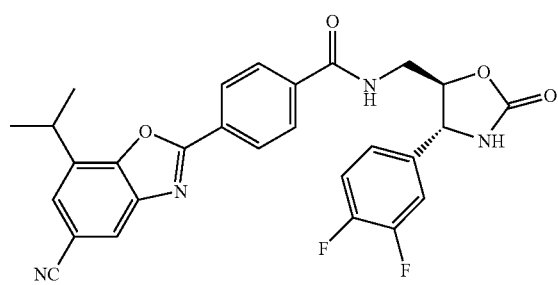 |
| 89 | 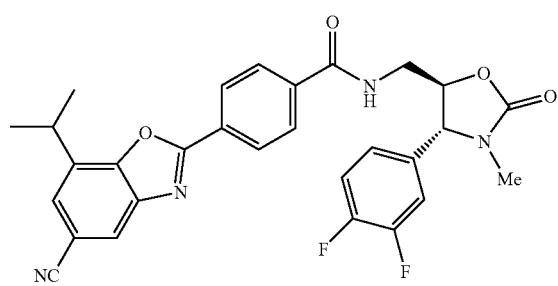 |
| 90 | 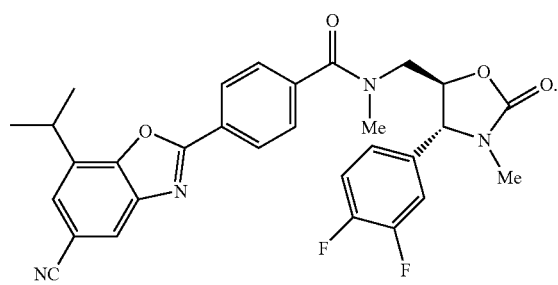 |

8. The compound of claim 1, which is selected from the group consisting of the following compounds, or a pharmaceutically acceptable salt thereof:
(a)
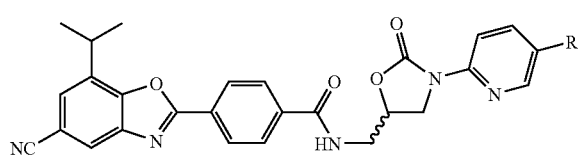
| EXAMPLE | wherein R is |
|---|---|
| 3 | 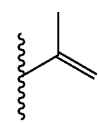 |
| 4 | 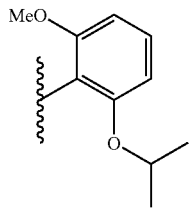 |
| 5 | 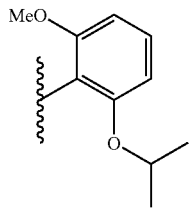 |
| 6 | 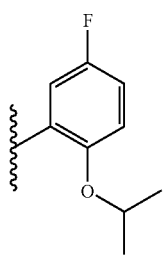 |
| 7 | 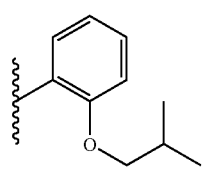 |
| 8 | 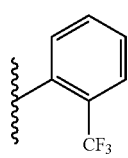 |
-continued
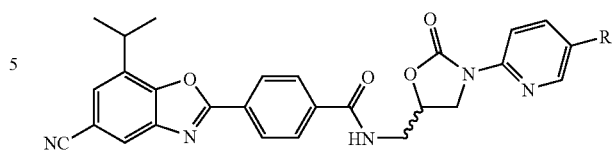
| EXAMPLE | wherein R is |
|---|---|
| 9 | 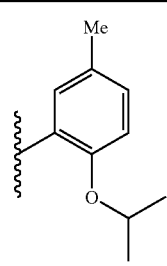 |
| 10 | 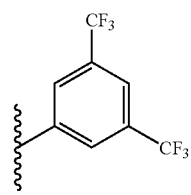 |
| 11 | 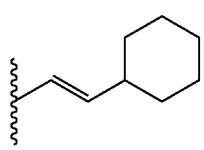 |
| 12 | 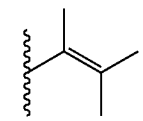 |
| 13 | 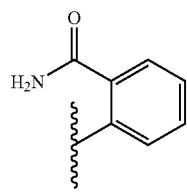 |
| 14 | 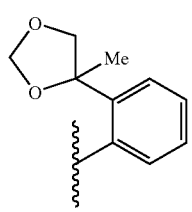 |
| 15 | 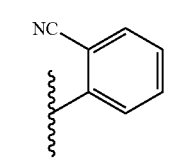 |

-continued

| EXAMPLE | wherein R is |
|---|---|
| 16 | 2-O₂N-phenyl |
| 17 | 2-(ethoxymethyl)phenyl |
| 18 | cyclopent-1-enyl |
| 19 | 5-methylthiophen-2-yl |
| 20 | 4-t-Bu-phenyl |
| 21 | 3-CF₃-phenyl |
| 22 | 2,6-dimethylphenyl |
| 23 | 2,4,5-trimethylphenyl |

-continued

| EXAMPLE | wherein R is |
|---|---|
| 24 | 3-(methoxycarbonyl)phenyl |
| 25 | 3-CN-phenyl |
| 26 | 1-phenylvinyl |

(b)

| EXAMPLE | wherein R is |
|---|---|
| 30 | 5-fluoro-2-isopropoxyphenyl |
| 31 | 5-fluoro-4-methoxy-2-isopropylphenyl |

-continued
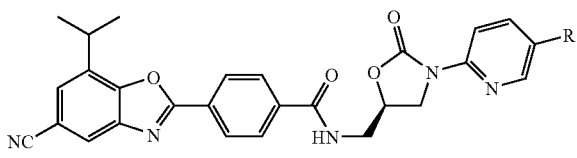
| EXAMPLE | wherein R is |
|---|---|
| 32 | 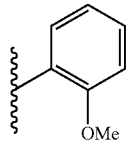 |
| 33 | 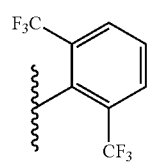 |
| 34 | 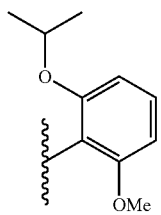 |
| 35 | 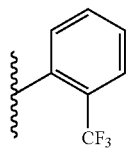 |
| 36 | 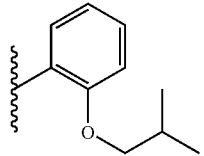 |
| 37 | 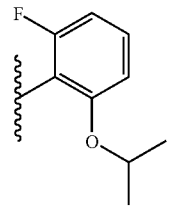 |
| 38 | 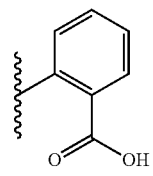 |
| 39 | 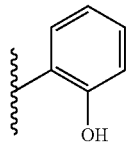 |
(c)
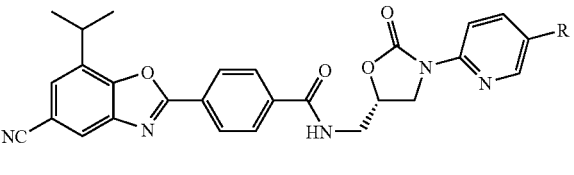
| EXAMPLE | wherein R is |
|---|---|
| 41 | 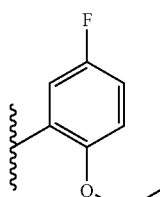 |
| 42 | 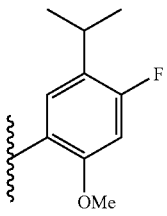 |
| 43 | 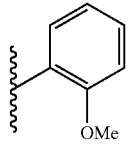 |
| 44 | 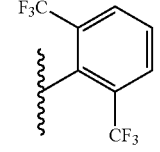 |
| 45 | 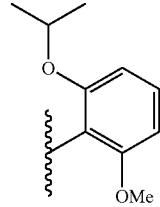 |
| 46 | 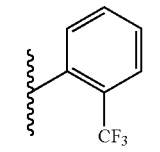 |
| 47 | 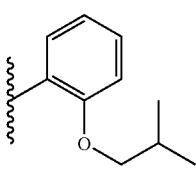 |

-continued
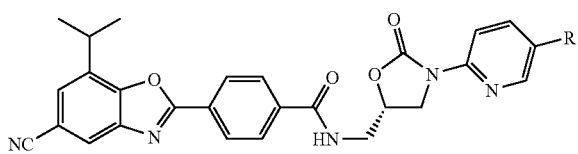
| EXAMPLE | wherein R is |
|---|---|
| 48 | 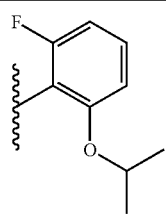 |
(d)
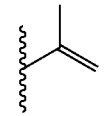
| EXAMPLE | wherein R is |
|---|---|
| 52 | 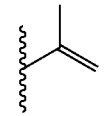 |
| 53 | 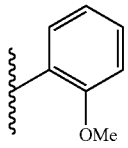 |
| 54 | 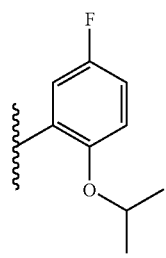 |
| 55 | 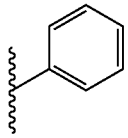 |
| 56 | 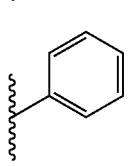 |
(e)
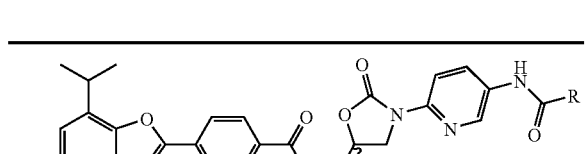
| EXAMPLE | wherein R is |
|---|---|
| 59 | 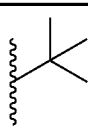 |
| 60 | 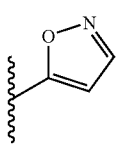 |
| 61 | 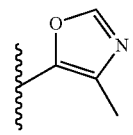 |
| 62 | 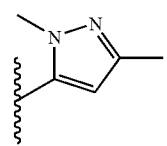 |
| 63 | 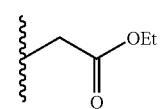 |
(f)
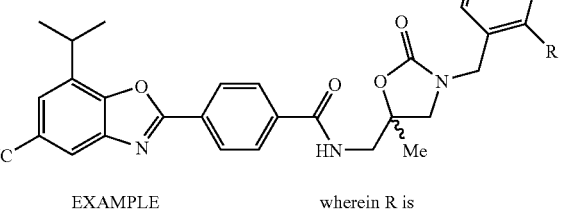
| EXAMPLE | wherein R is |
|---|---|
| 68 | 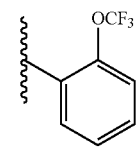 |
| 69 | 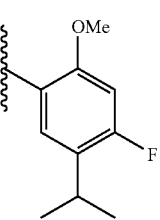 |

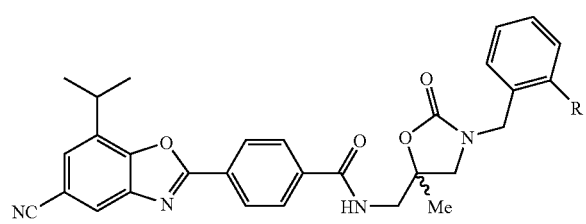
| EXAMPLE | wherein R is |
|---|---|
| 70 | 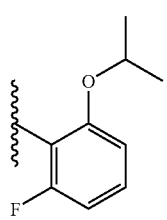 |
| 71 | 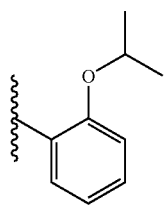 |
| 72 | 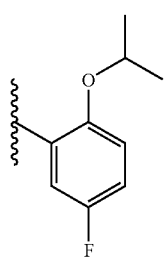 |
| 73 | 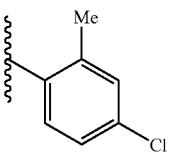 |
| 74 | 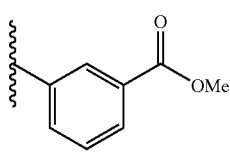 |
| 75 | 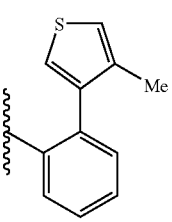 |
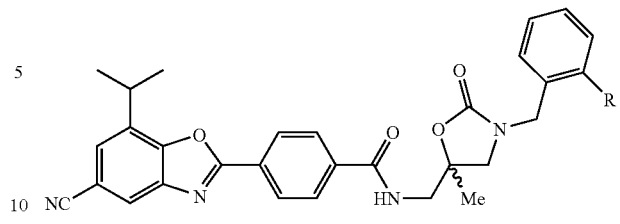
| EXAMPLE | wherein R is |
|---|---|
| 76 | 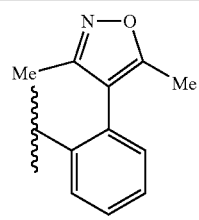 |
| 77 | 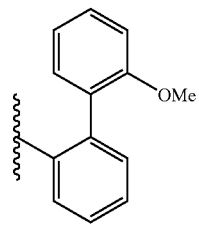 |
| 78 | 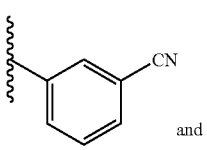 and |
(g)
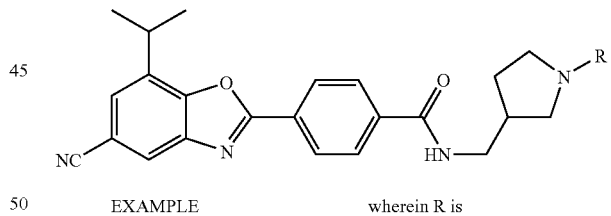
| EXAMPLE | wherein R is |
|---|---|
| 80 | 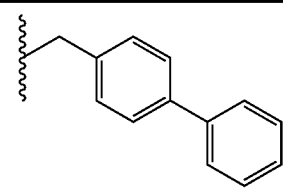 |
| 81 | 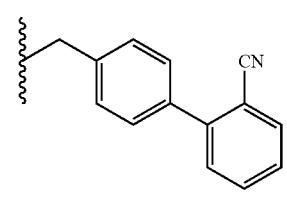 |

-continued

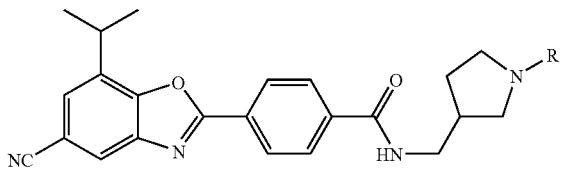

EXAMPLE | wherein R is
---|---
82 | 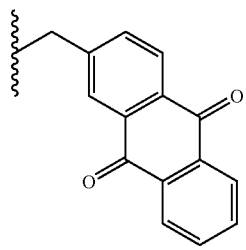
83 | 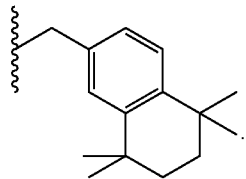

9. A method of treating atherosclerosis in a patient in need of treatment comprising the administration of a therapeutically effective amount of the compound of claim 1 to said patient, or a pharmaceutically acceptable salt thereof.

10. A method of raising HDL-C in a patient in need of treatment comprising the administration of a therapeutically effective amount of the compound of claim 1 to said patient, or a pharmaceutically acceptable salt thereof.

11. A method of lowering LDL-C in a patient in need of treatment comprising the administration of a therapeutically effective amount of the compound of claim 1 to said patient, or a pharmaceutically acceptable salt thereof.

12. A pharmaceutical composition comprising the compound of claim 1 or a pharmaceutically acceptable salt thereof, a pharmaceutically acceptable carrier, and one or more active ingredients selected from the group consisting of:
(i) HMG-CoA reductase inhibitors;
(ii) bile acid sequestrants;
(iii) niacin and related compounds;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression; and
(xvii) ileal bile acid transporters.

13. A pharmaceutical composition comprising the compound of claim 1 or a pharmaceutically acceptable salt thereof and pharmaceutically acceptable carrier.

* * * * *